(12) United States Patent
Stauffer et al.

(10) Patent No.: US 10,709,570 B2
(45) Date of Patent: Jul. 14, 2020

(54) IMPLANT WITH A DIAGONAL INSERTION AXIS

(71) Applicant: Institute for Musculoskeletal Science and Education, Ltd., King of Prussia, PA (US)

(72) Inventors: Megan A. Stauffer, Wayne, PA (US); Christopher J. Ryan, Lincoln University, PA (US); Edward J. McShane, III, Collegeville, PA (US); Joseph M. Nyahay, Eagleville, PA (US); Sean S. Bishop, Malvern, PA (US)

(73) Assignee: Institute for Musculoskeletal Science and Education, Ltd., King of Prussia, PA (US)

(*) Notice: Subject to any disclaimer, the term of this patent is extended or adjusted under 35 U.S.C. 154(b) by 56 days.

(21) Appl. No.: 15/884,845

(22) Filed: Jan. 31, 2018

(65) Prior Publication Data
US 2019/0038428 A1 Feb. 7, 2019

Related U.S. Application Data

(63) Continuation-in-part of application No. 15/334,053, filed on Oct. 25, 2016, which is a continuation of
(Continued)

(51) Int. Cl.
*A61F 2/44* (2006.01)
*A61F 2/30* (2006.01)

(52) U.S. Cl.
CPC ........ *A61F 2/4455* (2013.01); *A61F 2/30771* (2013.01); *A61F 2/442* (2013.01); *A61F 2002/30011* (2013.01); *A61F 2002/3092* (2013.01); *A61F 2002/3093* (2013.01); *A61F 2002/30289* (2013.01);
(Continued)

(58) Field of Classification Search
CPC ............................................ A61F 2/4455–447
See application file for complete search history.

(56) References Cited

U.S. PATENT DOCUMENTS 4,961,740 A  10/1990 Ray et al.
5,458,638 A  10/1995 Kuslich et al.
(Continued)

FOREIGN PATENT DOCUMENTS

CN 103932841 A 7/2014
WO 9848736 11/1998
(Continued)

OTHER PUBLICATIONS

International Search Report and Written Opinion for PCT application PCT/US2016/029865 dated Aug. 19, 2016.
(Continued)

*Primary Examiner* — Jacqueline T Johanas
(74) *Attorney, Agent, or Firm* — Plumsea Law Group, LLC

(57) ABSTRACT

An implant for insertion into a spine is configured with a body and a plurality of bone contacting elements. The implant is configured with an insertion axis that is diagonal to a lateral axis and to a posterior-anterior axis. The diagonal insertion axis allows for insertion of the implant using an oblique lumbar interbody fusion procedure.

7 Claims, 23 Drawing Sheets

Related U.S. Application Data application No. 15/141,655, filed on Apr. 28, 2016, now Pat. No. 9,918,849.

(60) Provisional application No. 62/301,546, filed on Feb. 29, 2016, provisional application No. 62/217,542, filed on Sep. 11, 2015, provisional application No. 62/154,599, filed on Apr. 29, 2015.

(52) U.S. Cl.
CPC .............. *A61F 2002/30593* (2013.01); *A61F 2002/30772* (2013.01); *A61F 2002/30774* (2013.01); *A61F 2002/30957* (2013.01); *A61F 2002/30985* (2013.01)

(56) References Cited

U.S. PATENT DOCUMENTS

| | | |
|---|---|---|
| 5,571,192 A | 11/1996 | Schonhoffer |
| 5,607,424 A | 3/1997 | Tropiano |
| 5,609,635 A | 3/1997 | Michelson |
| 5,658,337 A | 8/1997 | Kohrs et al. |
| 5,709,683 A | 1/1998 | Bagby |
| 5,716,416 A | 2/1998 | Lin |
| 5,897,556 A | 4/1999 | Drewry et al. |
| 6,010,502 A | 1/2000 | Bagby |
| 6,039,762 A | 3/2000 | McKay |
| 6,090,143 A | 7/2000 | Meriwether et al. |
| 6,126,689 A | 10/2000 | Brett |
| 6,149,651 A | 11/2000 | Drewry et al. |
| 6,200,348 B1 | 3/2001 | Biedermann et al. |
| 6,206,924 B1 | 3/2001 | Timm |
| 6,371,987 B1 | 4/2002 | Weiland et al. |
| 6,428,575 B2 | 8/2002 | Koo et al. |
| 6,436,141 B2 | 8/2002 | Castro et al. |
| 6,464,727 B1 | 10/2002 | Sharkey et al. |
| 6,494,883 B1 | 12/2002 | Ferree |
| 6,500,205 B1 | 12/2002 | Michelson |
| 6,520,996 B1 | 2/2003 | Manasas et al. |
| 6,527,805 B2 | 3/2003 | Studer et al. |
| 6,537,320 B1 | 3/2003 | Michelson |
| 6,582,431 B1 | 6/2003 | Ray |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,709,458 B2 | 3/2004 | Michelson |
| 6,758,849 B1 | 7/2004 | Michelson |
| 6,808,537 B2 | 10/2004 | Michelson |
| 6,846,327 B2 | 1/2005 | Khandkar et al. |
| 6,863,689 B2 | 3/2005 | Ralph et al. |
| 6,923,810 B1 | 8/2005 | Michelson |
| 6,962,606 B2 | 11/2005 | Michelson |
| 6,997,953 B2 | 2/2006 | Chung et al. |
| 7,141,068 B2 | 11/2006 | Ross et al. |
| 7,186,267 B2 | 3/2007 | Aston et al. |
| 7,261,739 B2 | 8/2007 | Ralph et al. |
| 7,341,601 B2 | 3/2008 | Eisermann et al. |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,485,134 B2 | 2/2009 | Simonson |
| 7,527,649 B1 | 5/2009 | Blain |
| 7,537,616 B1 | 5/2009 | Branch et al. |
| 7,621,952 B2 | 11/2009 | Truckai et al. |
| 7,621,953 B2 | 11/2009 | Braddock, Jr. et al. |
| 7,628,814 B2 | 12/2009 | Studer et al. |
| 7,794,500 B2 | 9/2010 | Felix |
| 7,799,056 B2 | 9/2010 | Sankaran |
| 7,803,191 B2 | 9/2010 | Biedermann et al. |
| 7,879,103 B2 | 2/2011 | Gertzman |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,062,365 B2 | 11/2011 | Schwab |
| 8,092,536 B2 | 1/2012 | Ahrens et al. |
| 8,142,507 B2 | 3/2012 | McGuckin, Jr. |
| 8,182,538 B2 | 5/2012 | O'Neil et al. |
| 8,226,718 B2 | 7/2012 | Castro |
| 8,241,363 B2 | 8/2012 | Sommerich et al. |
| 8,246,683 B2 | 8/2012 | Castro |
| 8,298,286 B2 | 10/2012 | Trieu |
| 8,328,848 B2 | 12/2012 | Lowery et al. |
| 8,361,149 B2 | 1/2013 | Castro |
| 8,414,820 B2 | 4/2013 | Bertele et al. |
| 8,430,930 B2 | 4/2013 | Hunt |
| 8,435,300 B2 | 5/2013 | Messerli et al. |
| 8,454,700 B2 | 6/2013 | Lemoine et al. |
| 8,475,533 B1 | 7/2013 | Castro |
| 8,551,173 B2 | 10/2013 | Lechmann et al. |
| 8,556,978 B2 | 10/2013 | Schaller |
| 8,613,769 B2 | 12/2013 | Sears et al. |
| 8,623,090 B2 | 1/2014 | Butler |
| 8,673,006 B2 | 3/2014 | Castro |
| 8,709,042 B2 | 4/2014 | Greenhalgh et al. |
| 8,728,160 B2 | 5/2014 | Globerman et al. |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,932,356 B2 | 1/2015 | Kraus |
| 8,940,052 B2 | 1/2015 | Lechmann et al. |
| 8,951,300 B2 | 2/2015 | Parrish |
| 8,986,383 B2 | 3/2015 | Castro |
| 9,011,499 B1 | 4/2015 | Kiester |
| 9,039,766 B1 | 5/2015 | Fonte |
| 9,060,876 B1 | 6/2015 | To et al. |
| 9,173,746 B2 | 11/2015 | Lowery et al. |
| 9,186,252 B2 | 11/2015 | Leibinger |
| 9,186,257 B2 | 11/2015 | Geisler et al. |
| 9,247,970 B2 | 2/2016 | Teisen |
| 9,271,845 B2 | 3/2016 | Hunt et al. |
| 9,295,562 B2 | 3/2016 | Lechmann et al. |
| 9,402,733 B1 | 8/2016 | To et al. |
| 9,408,651 B2 | 8/2016 | Sennett et al. |
| 9,421,108 B2 | 8/2016 | Hunt |
| 9,649,200 B2 | 5/2017 | Wickham |
| 2001/0014826 A1 | 8/2001 | Biedermann et al. |
| 2001/0032018 A1 | 10/2001 | Castro et al. |
| 2002/0052656 A1 | 5/2002 | Michelson |
| 2003/0078660 A1 | 4/2003 | Clifford et al. |
| 2003/0083746 A1 | 5/2003 | Kuslich |
| 2003/0109928 A1* | 6/2003 | Pasquet .............. A61F 2/4455 623/17.11 |
| 2004/0059419 A1 | 3/2004 | Michaelson |
| 2004/0122518 A1* | 6/2004 | Rhoda .................. A61F 2/44 623/17.11 |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0027364 A1 | 2/2005 | Kim et al. |
| 2005/0177238 A1 | 8/2005 | Khandkar et al. |
| 2005/0222681 A1 | 10/2005 | Richley et al. |
| 2005/0278027 A1 | 12/2005 | Hyde, Jr. |
| 2005/0278028 A1 | 12/2005 | Mujwid |
| 2006/0041262 A1 | 2/2006 | Calvert et al. |
| 2006/0052872 A1 | 3/2006 | Studer et al. |
| 2006/0100706 A1 | 5/2006 | Shadduck et al. |
| 2006/0147332 A1 | 7/2006 | Jones et al. |
| 2006/0212118 A1 | 9/2006 | Abernathie |
| 2006/0217806 A1* | 9/2006 | Peterman ............. A61F 2/4455 623/17.11 |
| 2006/0293753 A1 | 12/2006 | Thramann |
| 2007/0027544 A1 | 2/2007 | McCord et al. |
| 2007/0179610 A1 | 8/2007 | Biedermann et al. |
| 2007/0198090 A1 | 8/2007 | Abdou |
| 2007/0260324 A1 | 11/2007 | Joshi et al. |
| 2008/0071356 A1 | 3/2008 | Greenhalgh |
| 2008/0167686 A1 | 7/2008 | Trieu et al. |
| 2008/0306595 A1 | 12/2008 | McLeod et al. |

(56) References Cited

U.S. PATENT DOCUMENTS

| | | | |
|---|---|---|---|
| 2008/0312742 A1 | 12/2008 | Abernathie | |
| 2009/0030520 A1* | 1/2009 | Biedermann | A61B 17/8033 623/17.16 |
| 2009/0036985 A1 | 2/2009 | Whiting | |
| 2009/0048678 A1 | 2/2009 | Saal et al. | |
| 2009/0112321 A1 | 4/2009 | Kitchen | |
| 2009/0149958 A1 | 6/2009 | Prewett et al. | |
| 2009/0248162 A1 | 10/2009 | Peckham | |
| 2010/0016974 A1 | 1/2010 | Janowski et al. | |
| 2010/0152856 A1 | 6/2010 | Overes et al. | |
| 2010/0161061 A1 | 6/2010 | Hunt | |
| 2010/0286778 A1 | 11/2010 | Eisermann et al. | |
| 2011/0015741 A1 | 1/2011 | Melkent et al. | |
| 2011/0066192 A1 | 3/2011 | Frasier et al. | |
| 2011/0166660 A1 | 7/2011 | Laurence | |
| 2011/0190895 A1 | 8/2011 | Segal et al. | |
| 2011/0208311 A1 | 8/2011 | Janowski | |
| 2011/0245926 A1 | 10/2011 | Kitchen | |
| 2011/0270401 A1 | 11/2011 | McKay | |
| 2011/0301709 A1 | 12/2011 | Kraus et al. | |
| 2011/0313532 A1 | 12/2011 | Hunt | |
| 2012/0010472 A1* | 1/2012 | Spann | A61B 17/02 600/214 |
| 2012/0010717 A1* | 1/2012 | Spann | A61B 17/02 623/17.16 |
| 2012/0150300 A1 | 6/2012 | Nihalani | |
| 2012/0158143 A1* | 6/2012 | Shapiro | A61F 2/4455 623/17.16 |
| 2012/0191188 A1 | 7/2012 | Huang | |
| 2012/0191189 A1 | 7/2012 | Huang | |
| 2012/0239150 A1 | 9/2012 | Ullrich, Jr. et al. | |
| 2012/0296431 A1 | 11/2012 | Kim et al. | |
| 2013/0030529 A1 | 1/2013 | Hunt | |
| 2013/0096685 A1 | 4/2013 | Ciupik et al. | |
| 2013/0116793 A1 | 5/2013 | Kloss | |
| 2013/0123935 A1 | 5/2013 | Hunt et al. | |
| 2013/0158672 A1 | 6/2013 | Hunt | |
| 2013/0184826 A1 | 7/2013 | Thaiyananthan | |
| 2013/0190880 A1 | 7/2013 | Schaller | |
| 2013/0218282 A1 | 8/2013 | Hunt | |
| 2013/0218288 A1 | 8/2013 | Fonte et al. | |
| 2013/0304211 A1 | 11/2013 | Trautwein et al. | |
| 2014/0058513 A1 | 2/2014 | Gahman et al. | |
| 2014/0121776 A1 | 5/2014 | Hunt | |
| 2014/0142707 A1 | 5/2014 | Compton et al. | |
| 2014/0195005 A1 | 7/2014 | McKay | |
| 2014/0243980 A1 | 8/2014 | Sack et al. | |
| 2014/0249631 A1* | 9/2014 | Weiman | A61F 2/442 623/17.16 |
| 2014/0277457 A1 | 9/2014 | Yeung et al. | |
| 2014/0277464 A1 | 9/2014 | Richter et al. | |
| 2014/0277569 A1 | 9/2014 | Lange | |
| 2014/0288649 A1 | 9/2014 | Hunt | |
| 2014/0288650 A1 | 9/2014 | Hunt | |
| 2014/0303736 A1* | 10/2014 | Roussouly | A61F 2/4465 623/17.16 |
| 2014/0303745 A1 | 10/2014 | Anderson et al. | |
| 2014/0309743 A1 | 10/2014 | Falahee | |
| 2014/0336771 A1* | 11/2014 | Zambiasi | A61F 2/4455 623/17.16 |
| 2014/0358246 A1 | 12/2014 | Levy et al. | |
| 2015/0127106 A1 | 5/2015 | Partee et al. | |
| 2015/0173910 A1 | 6/2015 | Siegal et al. | |
| 2015/0282933 A1 | 10/2015 | Hunt | |
| 2015/0282945 A1 | 10/2015 | Hunt | |
| 2015/0282946 A1 | 10/2015 | Hunt | |
| 2016/0022430 A1 | 1/2016 | Wickham | |
| 2016/0045230 A1 | 2/2016 | Lowery et al. | |
| 2016/0081809 A1 | 3/2016 | Schneider et al. | |
| 2016/0193057 A1 | 7/2016 | Rhoda | |
| 2016/0206439 A1 | 7/2016 | To et al. | |
| 2016/0206440 A1 | 7/2016 | DeRidder et al. | |
| 2016/0310294 A1* | 10/2016 | McConnell | A61F 2/4455 |
| 2016/0317320 A1* | 11/2016 | Ahn | A61F 2/4455 |
| 2016/0324656 A1 | 11/2016 | Morris et al. | |
| 2017/0042697 A1 | 2/2017 | McShane, III et al. | |
| 2017/0095352 A1* | 4/2017 | Bruffey | A61F 2/442 |
| 2017/0156878 A1 | 6/2017 | Tsai et al. | |
| 2017/0156879 A1* | 6/2017 | Janowski | A61F 2/447 |
| 2017/0182222 A1* | 6/2017 | Paddock | A61F 2/44 |
| 2017/0348115 A1 | 12/2017 | Greenhalgh et al. | |
| 2018/0110626 A1* | 4/2018 | McShane, III | A61F 2/446 |
| 2018/0221156 A1* | 8/2018 | Jones | A61F 2/4455 |
| 2018/0243104 A1* | 8/2018 | Garonzik | A61F 2/447 |
| 2018/0280139 A1* | 10/2018 | Jones | A61F 2/4455 |
| 2018/0289503 A1* | 10/2018 | Knapp | A61B 17/8625 |
| 2018/0333272 A1* | 11/2018 | Mirda | A61F 2/4455 |
| 2019/0038428 A1* | 2/2019 | Stauffer | A61F 2/4455 |

FOREIGN PATENT DOCUMENTS

| | | |
|---|---|---|
| WO | 2002009625 A1 | 2/2002 |
| WO | 2003099160 A1 | 12/2003 |
| WO | 2009-051779 A1 | 4/2009 |
| WO | 2009051779 A1 | 4/2009 |
| WO | 2010-097632 A1 | 9/2010 |
| WO | 2011-159587 A1 | 12/2011 |
| WO | 2013-019543 A2 | 2/2013 |
| WO | 2017100366 A1 | 6/2017 |

OTHER PUBLICATIONS

International Search Report and Written Opinion dated Jan. 18, 2018 for International Patent Application No. PCT/US2017/58100.

"FDA Clears Camber Spine Technologies; 3D Printed SPIRA Open Matrix ALIF", Orthopedic Design & Technology, Aug. 15, 2017, https://www.odtmag.comjconents/view_breaking-news/2017-08-IS/fda-dears-camber-spine-technologies-3d-printed-spira-ope. Last accessed Dec. 15, 2017.

Office Action dated Apr. 3, 2019 for Chinese Application No. 201680039103.6.

International Search Report and Written Opinion dated Apr. 26, 2019 for International Application No. PCT/US2019/15946.

Office Action dated Jun. 28, 2019 in European Application No. 16722008.6-1132.

* cited by examiner

IMPLANT WITH A DIAGONAL INSERTION AXIS

RELATED APPLICATIONS

The present disclosure is a continuation-in-part of McShane III, U.S. Patent Publication Number 2017/0042697, currently U.S. application Ser. No. 15/334,053, filed Oct. 25, 2016, and titled "Implant With Arched Bone Contacting Elements," which application claims priority to Morris et al., U.S. Patent Publication Number 2016/0324656, currently U.S. application Ser. No. 15/141,655, filed Apr. 28, 2016 and titled "Coiled Implants and Systems and Methods Thereof," which application claims priority to U.S. Provisional Application No. 62/301,546, filed Feb. 29, 2016, U.S. Provisional Application No. 62/217,542, filed Sep. 11, 2015, and U.S. Provisional Application No. 62/154,599, filed Apr. 29, 2015. Each of the applications listed above are incorporated herein by reference in their entirety.

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

SUMMARY

In one aspect, an implant includes a body comprised of a peripheral structure, the body further comprising an opening for receiving part of an insertion device. The implant also includes a plurality of bone contacting elements attached to the body. The peripheral structure is further comprised of a first lateral portion, a second lateral portion, an anterior portion and a posterior portion. The first lateral portion and the anterior portion are joined at a first corner portion of the peripheral structure and wherein the second lateral portion and the posterior portion are joined at a second corner portion of the peripheral structure. The opening is disposed in the first corner portion of the peripheral structure.

In another aspect, an implant includes a body comprised of a peripheral structure and a support beam. The implant also includes a plurality of bone contacting elements attached to the body. The peripheral structure is further comprised of a first lateral portion, a second lateral portion, an anterior portion and a posterior portion. The first lateral portion and the anterior portion are joined at a first corner portion of the peripheral structure and wherein the second lateral portion and the posterior portion are joined at a second corner portion of the peripheral structure. The support beam has a first end attached to the first corner portion of the peripheral structure and the support beam has a second end attached to the second corner portion of the peripheral structure.

In another aspect, an implant includes a body comprised of a peripheral structure and a plurality of bone contacting elements attached to the body. The peripheral structure is further comprised of a first lateral portion, a second lateral portion, an anterior portion and a posterior portion. The first lateral portion and the anterior portion are joined at a first corner portion of the peripheral structure and the second lateral portion and the posterior portion are joined at a second corner portion of the peripheral structure. The second lateral portion and the anterior portion are joined at a third corner portion of the peripheral structure and the first lateral portion and the posterior portion are joined at a fourth corner portion of the peripheral structure. The plurality of bone contacting elements present a curved surface on a superior side of the device and where the curved surface curves from the third corner portion to the fourth corner portion.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

Figure 1:
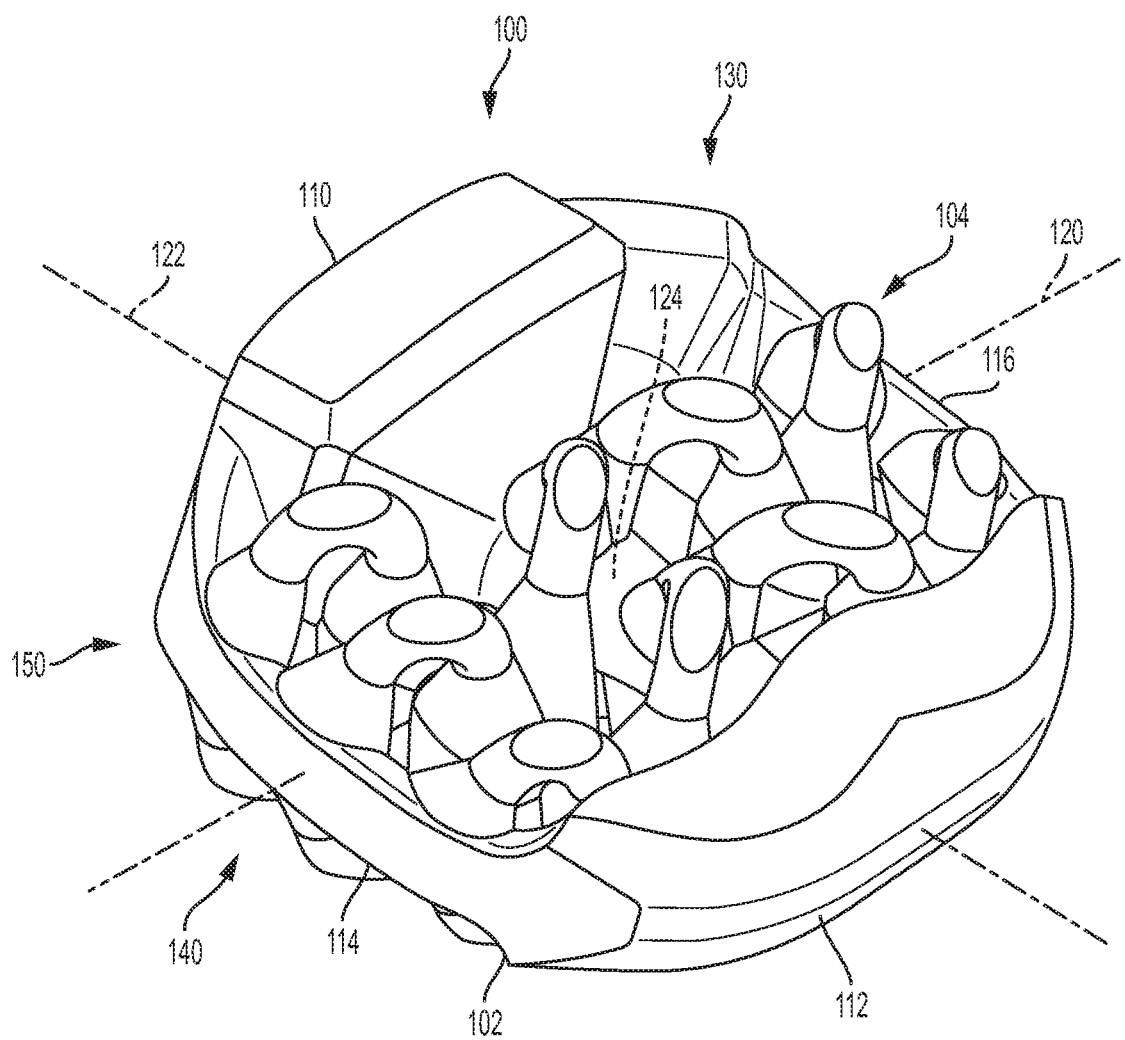
FIG. 1 is a schematic isometric view of an embodiment of an implant.

The embodiments described herein are directed to an implant for use in a spine. The embodiments include implants with a body and one or more arched bone contacting elements.

In addition to the various provisions discussed below, any embodiments may make use of any of the body/support structures, frames, plates, coils or other structures disclosed in McShane III et al., U.S. Publication Number 2018/0110626, published on Apr. 26, 2018, and titled "Implant with Protected Fusion Zones," which is hereby incorporated by reference in its entirety.

Also, any of the embodiments disclosed herein may make use of any of the body/support structures, elements, frames, plates or other structures disclosed in McShane III et al., U.S. Publication Number 2017/0042697, published on Feb. 16, 2017, and titled "Implant with Arched Bone Contacting Elements," and which is incorporated herein by reference in its entirety.

Also, any of the embodiments disclosed herein may make use of any of the body/support structures, elements, frames, plates or other structures disclosed in McShane III et al., U.S. Publication Number 2018/0256351, published on Sep. 13, 2018, and titled "Implant with Structural Members Arranged Around a Ring," and which is incorporated herein by reference in its entirety and referred to herein as "The Ring application."

Also, any embodiments may make use of any of the body/support structures, frames, plates or other structures disclosed in Morris et al., U.S. Publication Number 2016/0324656, published on Nov. 10, 2016, and titled "Coiled Implants and Systems and Methods of Use Thereof," which is hereby incorporated by reference in its entirety. For purposes of convenience, the Morris application will be referred to throughout the application as "The Coiled Implant Application".

Also, any of the embodiments disclosed herein may make use of any of the body/support structures, elements, frames, plates, or other structures disclosed in Nyahay et al., U.S. Pat. No. 10,357,377, issued on Jul. 23, 2019, and entitled "Implant with Bone Contacting Elements Having Helical and Undulating Planar Geometries," and which is incorporated herein by reference in its entirety.

Also, any of the embodiments disclosed herein may make use of any of the body/support structures, elements, frames, plates, or other structures disclosed in Nyahay et al., U.S. Publication Number 2018/0256353, published on Sep. 13, 2018, and entitled "Corpectomy Implant," and which is incorporated herein by reference in its entirety.

Also, any of the embodiments disclosed herein may make use of any of the body/support structures, elements, frames, plates, or other structures disclosed in Bishop et al., U.S. Pat. No. 10,213,317, issued on Feb. 26, 2019 and entitled "Implant with Supported Helical Members," and which is incorporated herein by reference in its entirety.

Also, any of the embodiments disclosed herein may make use of any of the body/support structures, elements, frames, plates, or other structures disclosed in Hamzey et al., U.S. Publication Number 2018/0296347, published on Oct. 18, 2018, and entitled "Implant with Curved Bone Contacting Elements," and which is incorporated herein by reference in its entirety.

Also, any of the embodiments disclosed herein may make use of any of the body/support structures, elements, frames, plates, or other structures disclosed in Hamzey et al., U.S. Publication Number 2018/0296350, published on Oct. 18, 2018, and entitled "Implant with Multi-Layer Bone Interfacing Lattice," and which is incorporated herein by reference in its entirety.

Introduction to Implant

Figure 2:
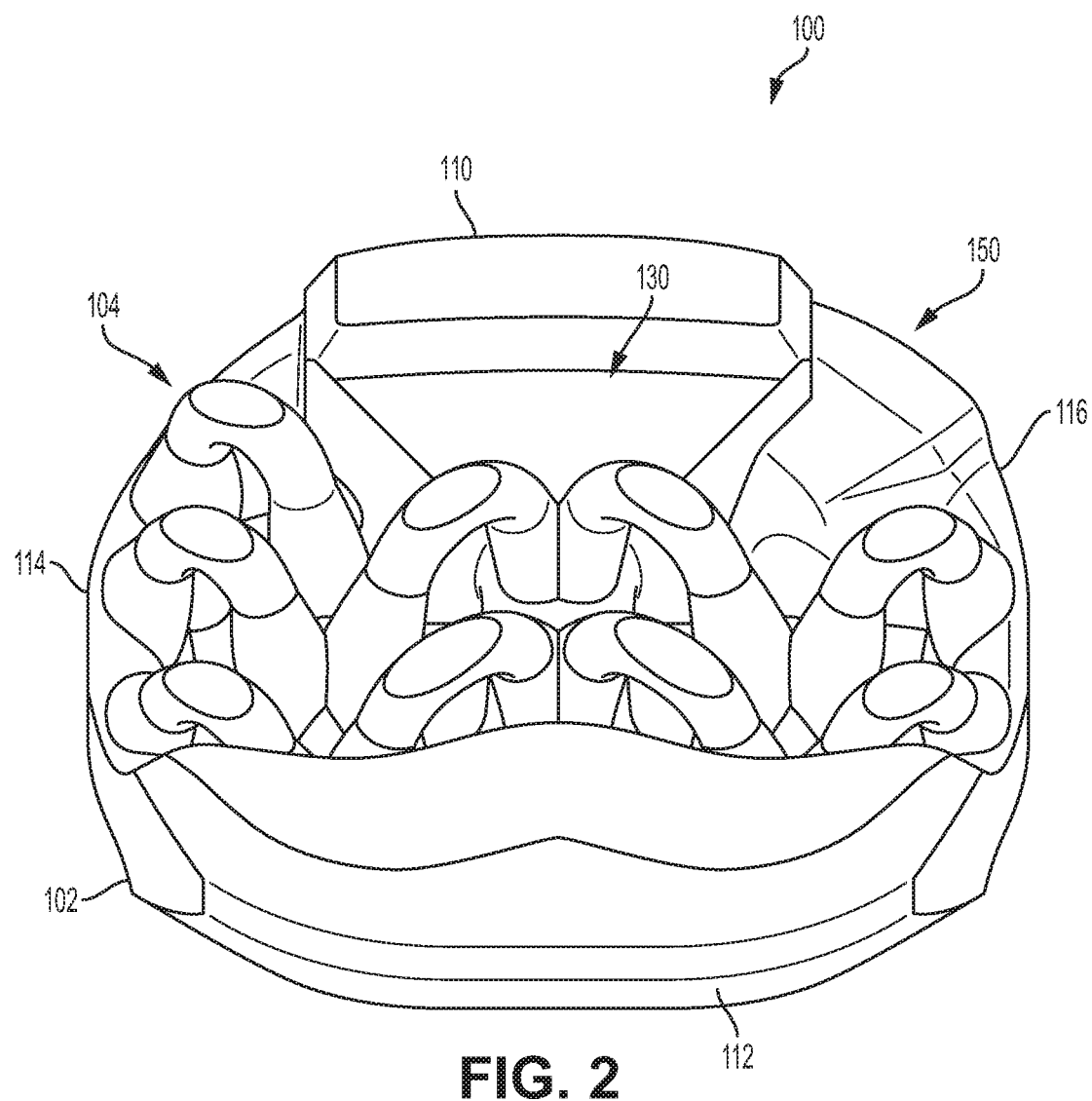
FIG. 2 is a schematic isometric view of an embodiment of an implant.
Figure 3:
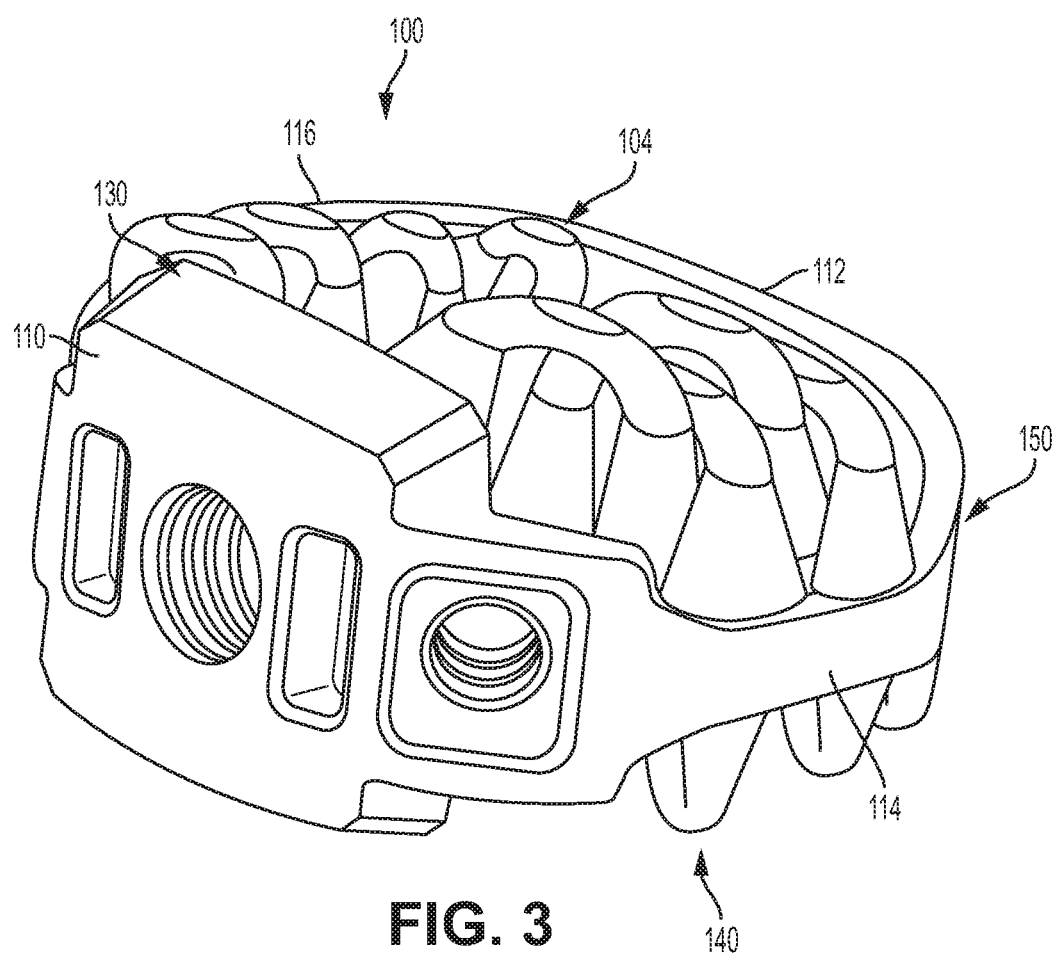
FIG. 3 is a schematic isometric view of an embodiment of an implant.

FIGS. 1-3 illustrate isometric views of an embodiment of implant 100. Implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, that is inserted between adjacent vertebrae to provide support and/or facilitate fusion between the vertebrae.

In some embodiments, implant 100 may include a body 102. Body 102 may generally provide a frame or skeleton for implant 100. In some embodiments, implant 100 may also include a plurality of arched bone contacting elements 104. Plurality of arched bone contacting elements 104 may be attached, and/or continuously formed (or "integrally formed") with, body 102.

As used herein, each arched bone contacting element comprises a distinctive member or element that spans a region or area of an implant. In some embodiments, these elements may overlap or intersect, similar to elements in a lattice or other 3D mesh structure. In other embodiments, the elements may not overlap or intersect. Some embodiments may use elements in which the length of the element is greater than its width and its thickness. For example, in embodiments where an element has an approximately circular cross-sectional shape, the element has a length greater than its diameter. In the embodiments seen in FIGS. 1-3, each arched bone contacting element is seen to have an approximately rounded or circular cross-sectional shape (i.e., the element has the geometry of a solid tube) along at least a portion of the element. However, in other embodiments, an element could have any other cross-sectional shape, including, but not limited to various polygonal cross-sectional shapes, as well as any other regular and/or irregular cross-sectional shapes. In some cases, for example, the cross-sectional shape of an arched bone contacting element could vary along its length (e.g., the diameter or shape could change along its length).

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides or portions facing along lateral directions of the body following implantation.

In FIGS. 1-3, implant 100 is understood to be configured with an anterior side 110 and a posterior side 112. Implant 100 may also include a first lateral side 114 and a second lateral side 116 that extend between the posterior side 112 and the anterior side 110 on opposing sides of implant 100. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 1, implant 100 may be associated with a lateral axis 120 that extends along implant 100 between first lateral side 114 and second lateral side 116. Additionally, implant 100 may be associated with a posterior-anterior axis 122 that extends between posterior side 112 and anterior side 110. Moreover, implant 100 may be associated with a vertical axis 124 that extends along the thickness dimension of implant 100 and which is generally perpendicular to both lateral axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the transverse plane.

Peripheral Structure

In some embodiments, a body may comprise a peripheral structure and one or more support beams that extend from the peripheral structure. A peripheral structure may be comprised of any number of plates, walls or similar structures. In some embodiments the peripheral structure could comprise a ring. In other words, in some embodiments, the peripheral structure could be a peripheral ring structure. As seen in FIGS. 1-3, body 102 may be further comprised of a peripheral structure 150. Peripheral structure 150 is seen to have a ring-like geometry.

Figure 4:
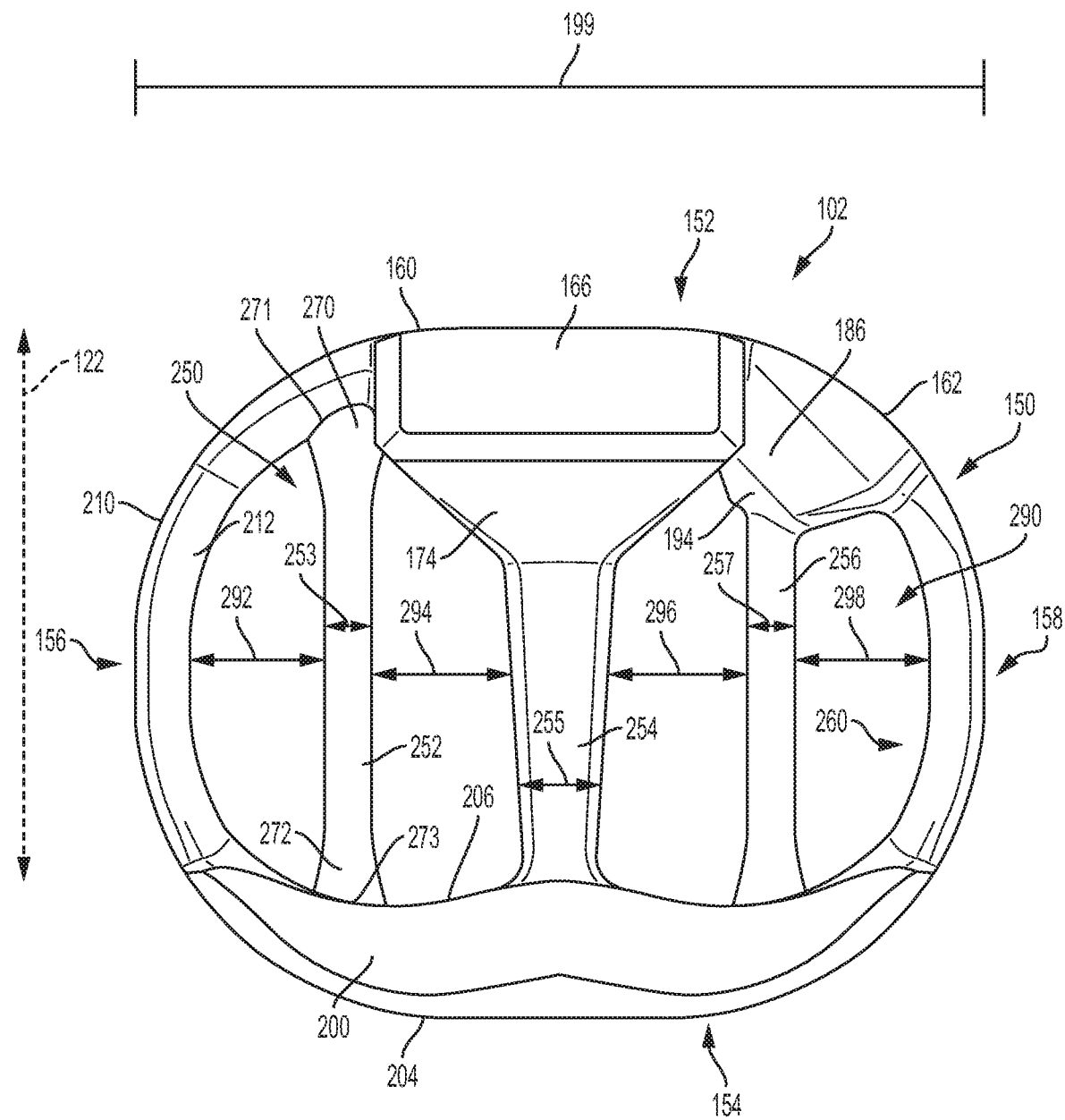
FIG. 4 is a schematic superior view of a body of the implant of FIG. 1.
Figure 5:
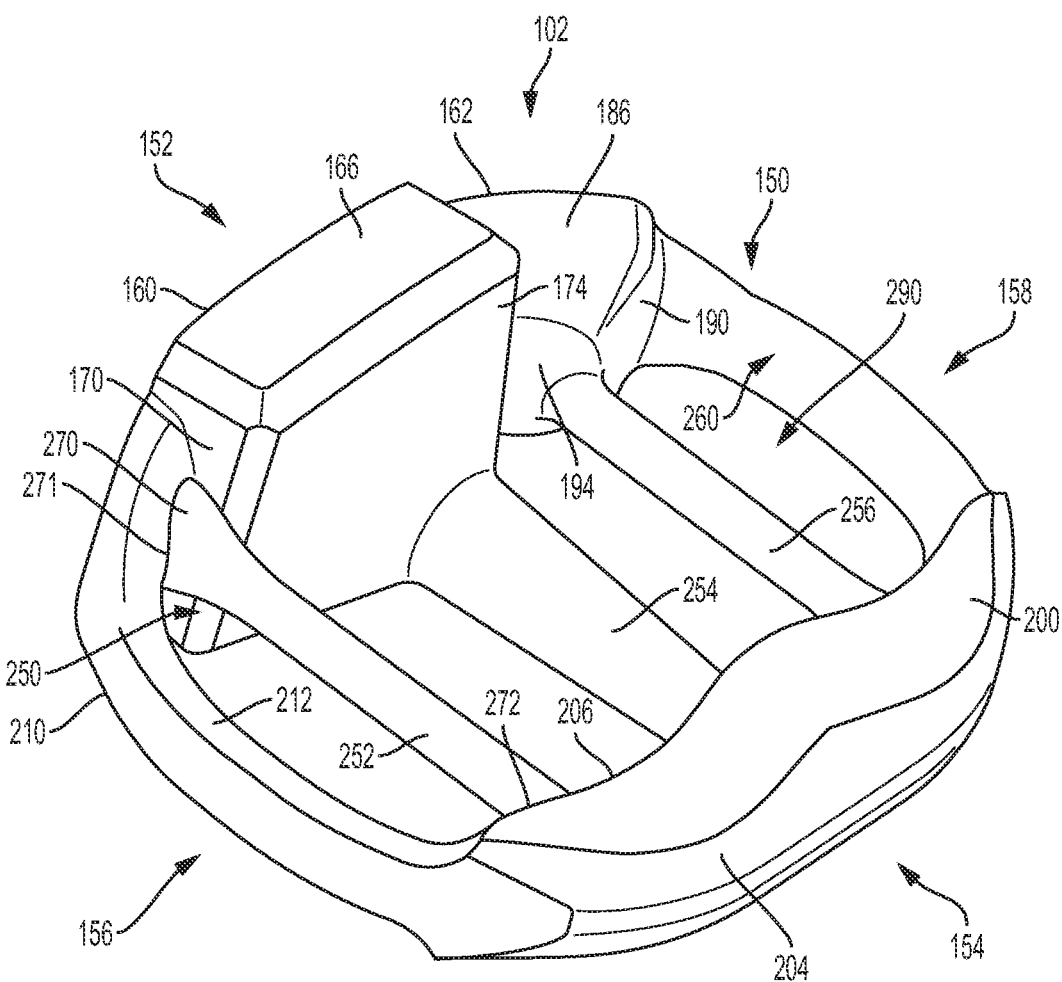
FIG. 5 is a schematic isometric view of the body of the implant of FIG. 4.

FIG. 4 is a schematic isometric view of body 102 shown in isolation without any arched bone contacting elements and FIG. 5 is a schematic top view of body 102 in isolation from any arched bone contacting elements. Referring to FIGS. 4-5, peripheral structure 150 may be further comprised of an anterior side 152, a posterior side 154, a first lateral side 156 and a second lateral side 158. As seen in FIGS. 1-2, in this exemplary embodiment, peripheral structure 150 is a continuous structure so that anterior side 152 is connected to first lateral side 156, first lateral side 156 is connected to posterior side 154, posterior side 154 is connected to second lateral side 158 and second lateral side 158 is connected to anterior side 152. That is, anterior side 152, first lateral side 156, posterior side 154 and second lateral side 158 together form a continuous or unbroken ring.

Figure 6:
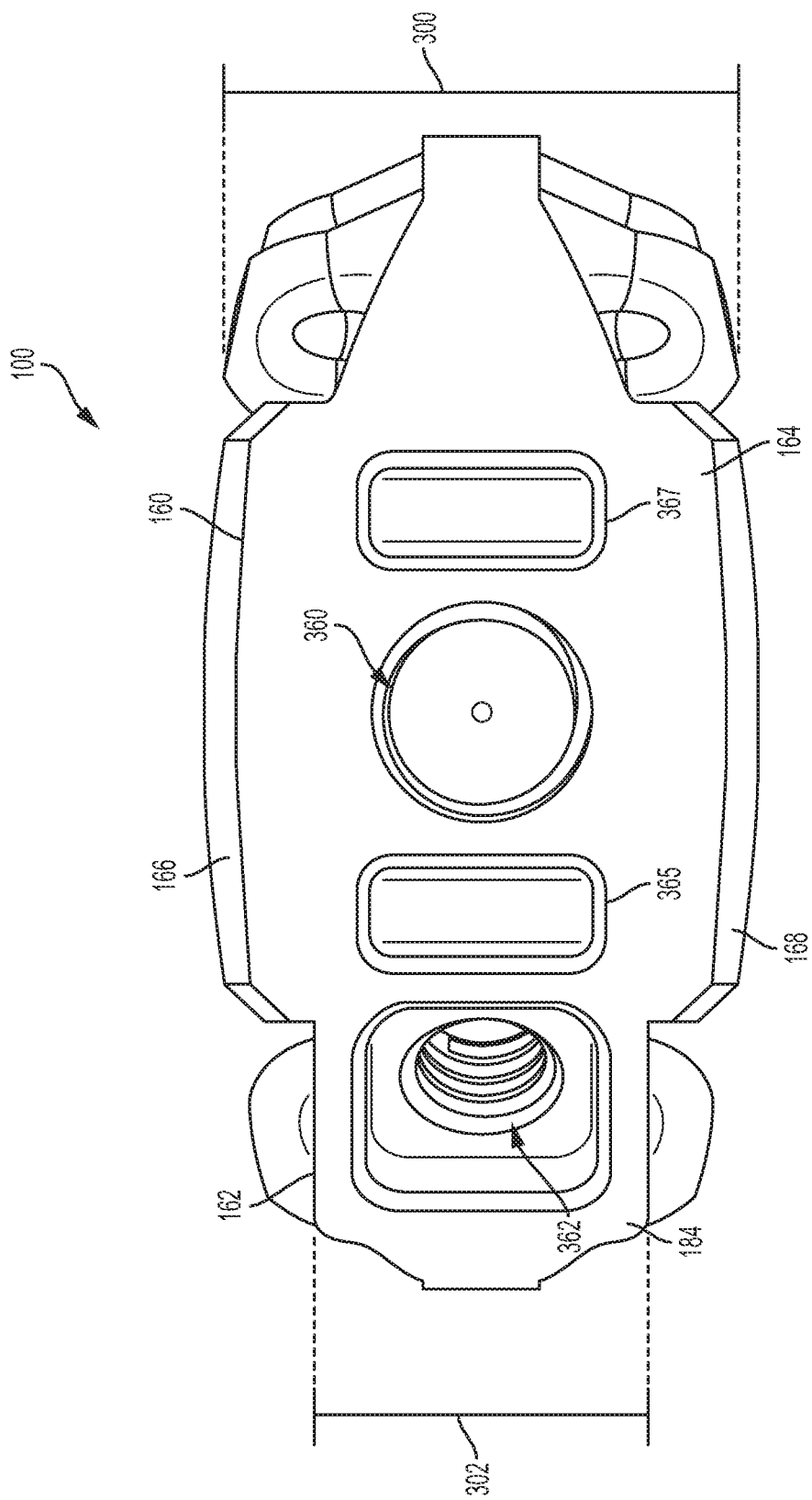
FIG. 6 is a schematic anterior view of an embodiment of an implant.
Figure 7:
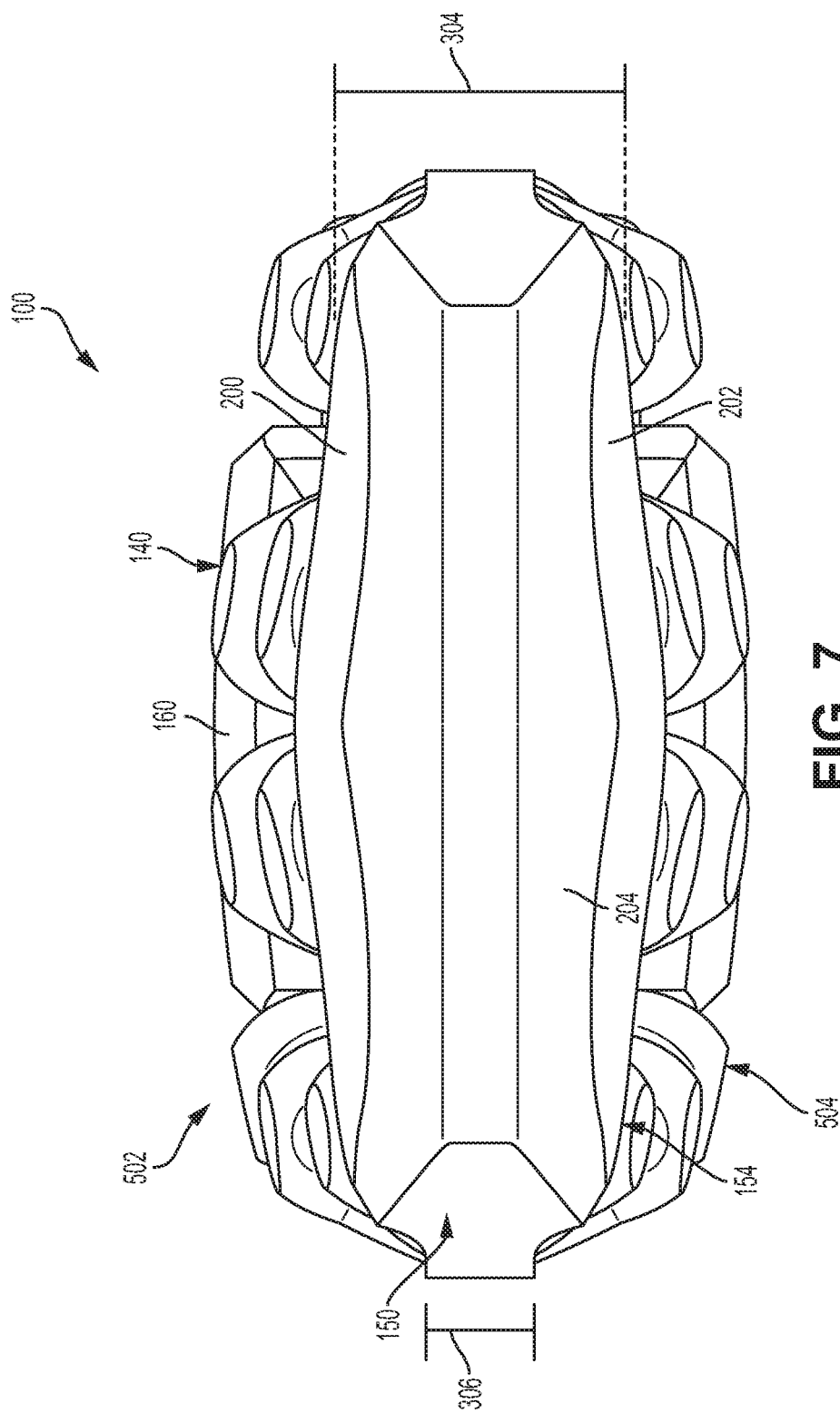
FIG. 7 is a schematic posterior view of an embodiment of an implant.

FIG. 6 is a schematic front view of implant 100 while FIG. 7 is a schematic rear view of implant 100. Referring now to FIGS. 4-7, anterior side 152 is further comprised of a first anterior portion 160 and a second anterior portion 162. First lateral side 156 extends from first anterior portion 160 of anterior side 152 to posterior side 154. Likewise, second lateral side 158 extends from second anterior portion 162 of anterior side 152 to posterior side 154.

First anterior portion 160 is comprised of a distal surface 164 (best seen in FIG. 6), a superior surface 166 and an inferior surface 168. First anterior portion 160 also includes a first lateral surface 170 and a second lateral surface (not shown) opposite first lateral surface 170. In addition, first anterior portion 160 includes a proximal surface 174 that is joined with a second support beam 254 as discussed below.

Second anterior portion 162 includes distal surface 184 (best seen in FIG. 6), a superior surface 186 and an inferior surface (not shown). Second anterior portion 162 also includes a first lateral surface 190 (see FIG. 5). In addition, second anterior portion 162 includes a proximal surface 194 that is joined with a third support beam 256 as discussed below. Moreover, second anterior portion 162 is disposed adjacent to first anterior portion 160. In some embodiments, first anterior portion 160 and second anterior portion 162 are joined together.

Each of first lateral side 156 and second lateral side 158 comprise a distal surface joined with a proximal surface. In some cases, the proximal surface may be convex. For example, first lateral side 156 includes distal surface 210 and proximal surface 212, where proximal surface 212 is convex and joined directly to distal surface 210 along the superior and inferior sides of implant 100.

Posterior side 154 of implant 100 comprises a superior surface 200 and an inferior surface 202 (see FIG. 7). Posterior side 154 also includes a distal surface 204 and a proximal surface 206. As seen in FIG. 5, the geometry of implant 100 at posterior side 154 tapers towards first lateral side 156 and second lateral side 158.

In some embodiments, the vertical height or thickness of different portions of a peripheral structure could vary. In the embodiment shown in FIG. 6, which shows a front schematic view of implant 100, first anterior portion 160 is shown to have a first height 300 while second anterior portion 162 is shown to have a second height 302. Here, first height 300 is seen to be greater than second height 302. In some embodiments, this tapering in height from the centrally located first anterior portion 160 to the adjacent second anterior portion 162 helps give anterior side 152 of peripheral structure 150 a convex shape to better fit between adjacent vertebral bodies upon implantation.

Furthermore, as seen in FIG. 7, the height of peripheral structure 150 along posterior side 154 is indicated as third height 304. In the exemplary embodiment, third height 304 is less than first height 300. Moreover, in some cases, third height 304 may be slightly less than second height 302. In some embodiments, variations in height or vertical thickness between the posterior and anterior sides of an implant may allow for an implant with hyper-lordotic angles between the inferior and superior surfaces. In other embodiments, variations in vertical thickness may be used to control the relative rigidity of the device in different locations.

In some embodiments, the thickness of peripheral structure 150 may be smaller along both of first lateral side 156 and second lateral side 158 than along either of anterior side 152 or posterior side 154. In the exemplary embodiment first lateral side 156 and second lateral side 158 have a similar fourth height 306. Here, fourth height 306 is less than first height 300, second height 302 and third height 304. By using a reduced height or vertical thickness for the lateral sides as compared to the anterior and posterior sides, it is possible to attach arched bone contacting elements to the lateral sides while maintaining a smooth vertical profile across the superior and inferior surfaces of implant 100 (see FIG. 7).

Support Beams

In some embodiments, a body may be provided with one or more support beams (or support structures) that act to reinforce a peripheral structure. In some embodiments, one or more support beams could be disposed along the interior of a peripheral structure. For example, in some embodiments, one or more support beams could extend from a first location on an inwardly (or proximally) facing surface of the support structure to a second location on the inwardly facing surface of the support structure. In other words, in some embodiments, one or more support beams may span an interior region bounded by the peripheral structure.

As seen in FIGS. 4-5, body 102 includes a plurality of support beams 250. These include first support beam 252, second support beam 254 and third support beam 256. In the embodiment shown in FIGS. 4-5, each of these support beams extends from a first location on inwardly facing surface 260 of peripheral structure 150 to a second location on an inwardly facing surface of peripheral structure 150. Here, it may be understood that the inwardly facing surface 260 of peripheral structure 150 is comprised of the proximal surfaces of the various sides of peripheral structure 150 (e.g., proximal surface 174, proximal surface 194, proximal surface 212, etc.).

Referring to FIGS. 4-5, first support beam 252 includes a first end 270 attached to a first anterior location 271 of inwardly facing surface 260 and a second end 272 attached at a second anterior location 273 of inwardly facing surface 260. Likewise, each of second support beam 254 and third support beam 256 include opposing ends attached to different locations along inwardly facing surface 260. With this arrangement, plurality of support beams 250 are seen to span an interior region 290 (or central region) that is bounded by peripheral structure 150.

The plurality of support beams 250 may be characterized as being centrally located within implant 100 with respect to peripheral structure 150. As used herein, "centrally located" does not refer to a precise location that is at the geometric center or center of mass of an implant, but rather a general area or region disposed inwardly of a peripheral structure (e.g., within interior region 290). Thus, in the following description and in the claims, a support beam may be referred to as a central beam.

In different embodiments, the number of support beams could vary. In some embodiments, a single support beam could be used. In other embodiments, two or more support beams could be used. In the exemplary embodiment shown in FIGS. 4-5, three support beams are used.

In different embodiments, the orientation of one or more beams could vary. In some embodiments, two or more support beams could be oriented in parallel. In other embodiments, two or more support beams could be disposed at oblique angles to one another. In the exemplary embodiment, first support beam 252, second support beam 254 and third support beam 256 may be disposed in parallel to one another. Moreover, in the exemplary embodiment, plurality of support beams 250 may be oriented in a posterior-anterior direction (i.e., along posterior-anterior axis 122). Of course, in other embodiments, plurality of support beams 250 could be oriented in any other directions.

In different embodiments, the spacing, or separation, between adjacent support beams could vary. In some embodiments, the spacing between adjacent support beams could be small relative to the lateral width of an implant. For example, the spacing could range between 0% and 10% of the width of an implant. In other embodiments, the spacing between adjacent support beams could be large relative to the width of an implant. For example, the spacing could range between 10% and 95% of the width of an implant (for example, two beams located adjacent to opposing lateral sides of the implant may could be spaced apart by 95% of the width of the implant). The spacing between adjacent beams (or between a beam and a portion of a peripheral structure) may be constant or may vary across an implant.

It may be appreciated that the relative spacing between support beams may be selected according to many factors, including the thicknesses of one or more support beams, the number of support beams used, the desired strength to weight ratio for an implant as well as other factors. Moreover, the spacing between adjacent support beams may be determined according to the dimensions of one or more arched bone contacting elements, since the arched bone contacting elements extend between adjacent support beams (or between a support beam and the peripheral structure).

In the embodiment shown in FIG. 4, first support beam 252 is spaced apart from first lateral side 156 by a spacing 292. First support beam 252 and second support beam 254 are spaced apart from one another by a spacing 294. Second support beam 254 and third support beam 256 are spaced apart from one another by a spacing 296. Third support beam 256 is spaced apart from second lateral side 158 by spacing 298. In the exemplary embodiment, each of spacing 292, spacing 294, spacing 296 and spacing 298 generally have a value in the range between 15% and 30% of width 199 of implant 100. Of course it may be appreciated that each spacing is an average or approximate spacing, since the spacing between adjacent components can vary, for example, along posterior-anterior axis 122.

In different embodiments, the geometry of one or more support beams could vary. In some embodiments, one or more support beams could have a curved geometry. In other embodiments, one or more support beams could have a substantially straight geometry. In the embodiment shown in FIGS. 4-5, each of plurality of support beams 250 has a substantially straight geometry. Moreover, the cross-sectional geometry of each support beam is substantially rounded. However, in other embodiments, one or more support beams could have any other cross-sectional shape, including but not limited to: rectangular shapes, polygonal shapes, regular shapes and/or irregular shapes. The cross-sectional shapes could also vary across a length of a support beam from, for example, a rounded cross-sectional shape (e.g., circular or elliptic) to a polygonal cross-sectional shape (e.g., rectangular).

In different embodiments, the thickness of one or more support beams could vary. Generally, the thickness (or diameter) of a support beam could vary in a range between 1% and 95% of the width (or length) of an implant. In the exemplary embodiment, first support beam 252, second support beam 254 and third support beam 256 have diameters in a range approximately between 2% and 15% of width 199 of implant 100, as seen in FIG. 4. More specifically, second support beam 254 has a diameter 255 that is greater than a diameter 253 of first support beam 252 and also that is greater than a diameter 257 of third support beam 256. In some cases, second support beam 254 may have the largest diameter. Because impact forces are applied at the center of implant 100 (where second support beam 254 is located) by a device coupled to implant 100 at first interior portion 160, this greater diameter for second support beam 254 may help reinforce the center of implant 100.

In at least some embodiments, support beams in the body of an implant may be coplanar. In FIGS. 4-5, first support beam 252, second support beam 254 and third support beam 256 are seen to reside in a similar plane of implant 100. The coplanar arrangement of support beams may help provide a generally symmetric arrangement for implant 100 between the superior and inferior sides.

Generally, the geometry of one or more portions of the body of an implant could vary from one embodiment to another. For example, portions of a body can include one or more windows, slots and/or openings that may facilitate bone growth through the implant and/or may reduce weight.

Fastening Provisions

Some embodiments can include one or more fastener receiving provisions. Some embodiments can include one or more attachment openings that may engage an insertion or implantation device. In some embodiments, an implant can include one or more threaded cavities. In some embodiments, a threaded cavity can be configured to mate with a corresponding threaded tip on an implantation tool or device. In other embodiments, a threaded cavity can receive a fastener for purposes of fastening an implant to another device or component in an implantation system that uses multiple implants and/or multiple components.

As best seen in FIG. 6, implant 100 includes a first threaded cavity 360 disposed in first anterior portion 160. Implant 100 also includes second threaded cavity 362 disposed in second anterior portion 162. In some embodiments, first threaded cavity 360 may receive the threaded tip of an implantation tool (not shown). Such a tool could be used to drive implant 100 between adjacent vertebral bodies. Optionally, in some cases, implant 100 may also include a pair of indentations (indentation 365 and indentation 367) that may facilitate alignment between an implantation tool and implant 100. In some embodiments, second threaded cavity 362 could be used to fasten implant 100 to a separate component (not shown) of a broader implantation system. For example, some embodiments could incorporate a separate plate that may be fastened to implant 100 using a fastener secured within second threaded cavity 362. Such a plate could include additional fixation members (e.g., screws) that could be used with the implant.

Arched Bone Contacting Elements

In some embodiments, an arched bone contacting element may include a first end portion, an intermediate portion and a second end portion. In some embodiments, the intermediate portion may have an arched geometry. In such cases, an intermediate portion having an arched geometry may be referred to as an "arched portion". In some embodiments, the first end portion and/or the second end portion could have a flared geometry. In such cases, an end having a flared geometry may be referred to as a "flared leg" of the arched bone contacting element.

Figure 8:
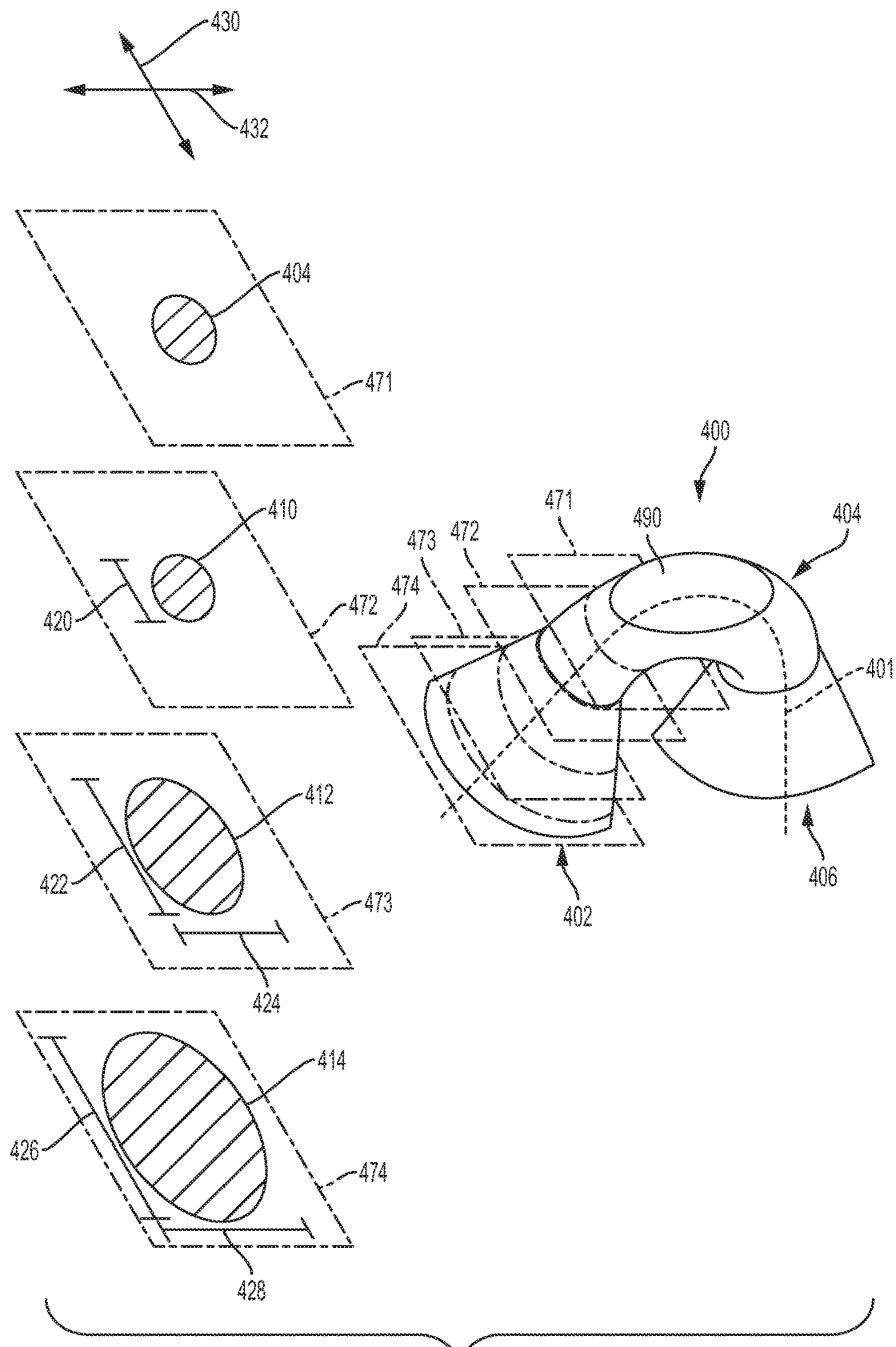
FIG. 8 is a schematic view of an arched bone contacting element including several schematic cross-sections, according to an embodiment.

FIG. 8 is a schematic view of an exemplary arched bone contacting element seen in isolation, including several enlarged schematic cross-sectional views taken at various locations of the element. Referring to FIG. 8, arched bone contacting element 400 is comprised of a first end portion, which is referred to as a first flared leg 402. Arched bone contacting element 400 is also comprised of an arched portion 404. Additionally, arched bone contacting element 400 is comprised of a second end portion, which is referred to as a second flared leg 406.

In some embodiments, an arched bone contacting element can include provisions for engaging a vertebral body following implantation. In some embodiments, one or more arched bone contacting elements can include at least one distal surface region that is configured to directly contact a vertebral endplate. In some cases, a distal surface region could be a flattened surface region. In other cases, a distal surface region could be a convex surface region. In still other cases, a distal surface region could be a concave surface region. More generally, a distal surface region could have a different curvature from the adjacent surface regions of an arched portion. Moreover, the particular curvature for a distal surface region could be selected to match the local geometry of an opposing vertebral endplate.

As an example, in FIG. 8, arched bone contacting element 400 is seen to include a distal surface region 490 that is located in arched portion 404. In some embodiments, distal surface region 490 may have a convex curvature that is smaller than the curvature of adjacent regions of arched portion 404. Similarly, as best seen in FIG. 7, the remaining arched bone contacting elements of implant 100 are also configured with distal bone contacting regions having a smaller curvature than adjacent surface regions of arched portion 404 (i.e., these distal surface regions may be flatter than the remaining regions of arched portion 404, but may not be completely flat). Together, these distal bone contacting regions provide a partial smooth surface that can engage a vertebral body. Moreover, in some embodiments, the collection of flattened (or convex) bone contacting regions together form a minimal contact surface with the bone and thereby allow for an increased amount of graft material or bone growth promoting material to be placed in direct contact with the bone. Specifically, bone growth promoting material that is disposed in between arched bone contacting elements, including being disposed in the open regions along the superior and inferior surfaces, may directly contact the bone.

For purposes of reference, arched bone contacting element 400 may be characterized as having a curved central axis 401. As used herein, the curved central axis of an element is an axis that extends along the length of the element and is located at an approximate center of the element at each location along its length. It may be understood that the cross-sections discussed below and shown in FIG. 8 are taken along planes that are perpendicular to curved central axis 401.

As seen in FIG. 8, arched portion 404 has an arched geometry. Arched portion 404 is also seen to have a rounded cross-sectional shape. More specifically, in some cases, arched portion 404 has an approximately circular (or near-circular) cross-sectional shape. In some embodiments, the diameter and cross-sectional shape of arched portion 404 stays relatively constant along much of the length of arched portion 404 (i.e., along curved central axis 401). However, it may be understood that the cross-sectional shape of arched portion 404 could vary, for example, along flattened bone contacting region 490. For reference, a cross-section of arched portion 404 taken at reference plane 471 is shown in FIG. 8. Of course, in other embodiments, arched portion 404 could have any other cross-sectional shape.

At each flared leg, the cross-sectional shape of arched bone contacting element 400 may vary. For example, as seen in FIG. 8, the cross-sectional shape of first flared leg 402 has a first cross-sectional shape 410 at a location adjacent arched portion 404 (taken at reference plane 472). First flared leg 402 also has a second cross-sectional shape 412 and a third cross-sectional shape 414. Here, the third cross-sectional shape 414 is taken at a location furthest from arched portion 404 (taken at reference plane 474), and second cross-sectional shape 412 is taken at an intermediate location along first flared leg 402 (taken at reference plane 473).

As shown in FIG. 8, the cross-sectional shape of first flared leg 402 varies from an approximately circular cross-sectional shape (i.e., first cross-sectional shape 410) to an approximately elliptic cross-sectional shape (i.e., third cross-sectional shape 414). For example, the first cross-sectional shape 410 of first flared leg 402 has a similar diameter 420 along both a first axis 430 and a second axis 432. However, the second cross-sectional shape 412 has a major diameter 422 along first axis 430 that is greater than its minor diameter 424 along second axis 432. Furthermore, the third cross-sectional shape 414 also has a major diameter 426 along first axis 430 and a minor diameter 428 along second axis 432, where major diameter 426 is greater than major diameter 422 and minor diameter 428 is greater than minor diameter 424. Thus, the cross-sectional size of first flared leg 402 increases as its shape also changes from an approximately circular shape to an approximately elliptic shape.

With the arrangement described above, the cross-sectional area of arched bone contacting element 400 may be a minimum in arched portion 404. Moreover, moving along curved central axis 401 from arched portion 404 to first flared leg 402, the cross-sectional area increases through first flared leg 402 until reaching a maximum at the furthest end of first flared leg 402 (and similarly reaching a maximum at the furthest end of second flared leg 406).

Figure 9:
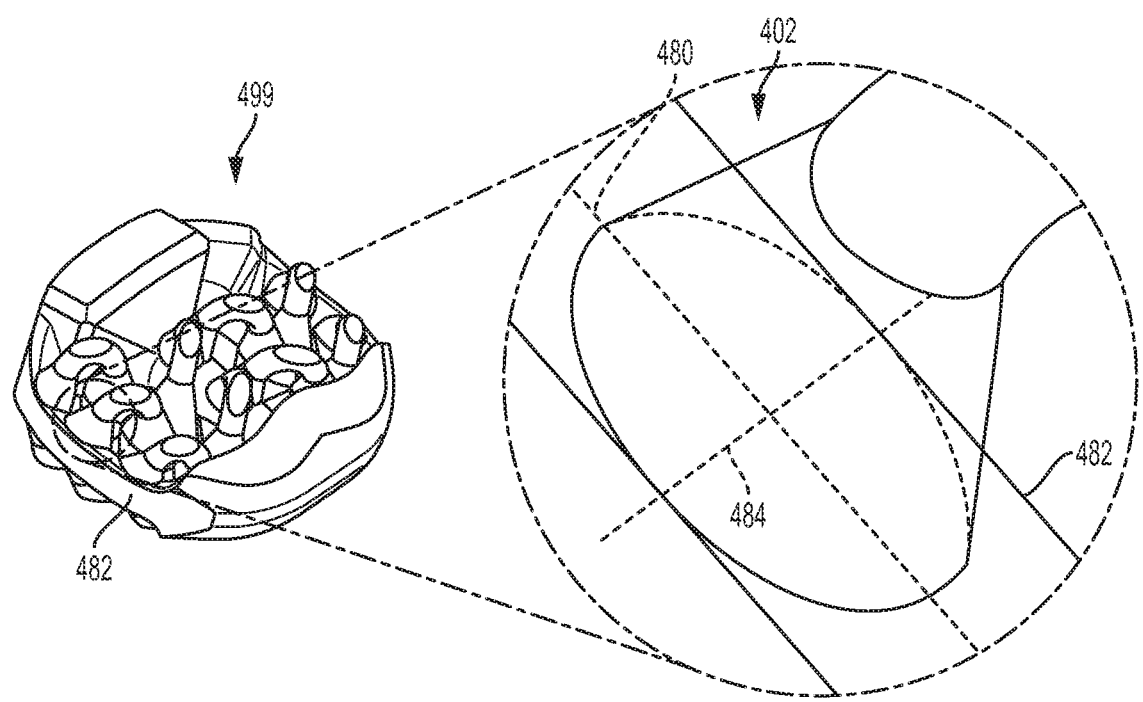
FIG. 9 is a schematic view of an implant including an enlarged schematic view of the attachment region between an arched bone contacting element and a portion of a body of the implant, according to an embodiment.

This increase in cross-sectional area provides for a wider base for each arched bone contacting element at its attachment to the body and can thus improve the strength of the attachment between the arched bone contacting element and the body. Moreover, the variation in cross-sectional shape allows the increase in size to be primarily directed in a direction parallel with the underlying structure (e.g., a support beam or a section of the peripheral structure). For example, as seen in FIG. 9, first flared leg 402 has a longest dimension parallel with a central axis 480 of peripheral segment 482 to which first flared leg 402 is attached. Here, peripheral segment 482 is a segment of implant 499. Moreover, first flared leg 402 has a smallest dimension parallel with a widthwise axis 484 of peripheral segment 482. Thus, the surface area of the attachment between arched bone contacting element 400 and peripheral segment 482 is increased while preventing first flared leg 402 from extending beyond peripheral segment 482 in the direction of widthwise axis 484.

While the geometry of first flared leg 402 is discussed in detailed, it may be appreciated that second flared leg 406 may have a similar geometry to first flared leg 402. Likewise, the flared legs of the remaining arched bone contacting elements of implant 100 may also have similar geometries to first flared leg 402.

The particular cross-sectional geometries (circular and elliptic) illustrated for portions of an arched bone contacting element in FIG. 8 are only intended to be schematic representations of possible variations in geometry for an arched bone contacting element. In some embodiments, a flared leg could have a more irregular geometry, which while increasing in size and becoming elongated along one axis, does not have a substantially elliptic cross-sectional shape. Moreover, the cross-sectional shape could change between any two shapes at opposing ends of the flared leg. Exemplary cross-sectional shapes include, but are not limited to: rounded (including circular and elliptic), rectangular, polygonal, regular, irregular as well as any other shapes.

Embodiments could include any number of arched bone contacting elements. Some embodiments may include a single arched bone contacting element. Still other embodiments could include any number of arched bone contacting elements in the range between 2 and 50. In still further embodiments, an implant could include more than 50 elements. In the exemplary embodiment shown in FIGS. 1-3, implant 100 includes 18 arched bone contacting elements, including nine elements on superior side 130 and nine elements on inferior side 140. The number of arched bone contacting elements used can vary according to factors including implant size, desired implant strength, desired volume for bone graft or other bone growth promoting materials as well as possibly other factors.

In different embodiments, the arrangement of arched bone contacting elements in an implant could vary. In some embodiments, arched bone contacting elements could attach to any portions of a peripheral structure, to any beams of an implant, as well as other arched bone contacting elements. In some embodiments, an arched bone contacting element could extend across the entire width of an implant. In other embodiments, an arched bone contacting element may only extend across a portion of the width of an implant.

In order to enhance strength in an implant, some embodiments may use arched bone contacting elements that only extend between adjacent beams or between a beam and an adjacent portion of a peripheral structure.

Figure 10:
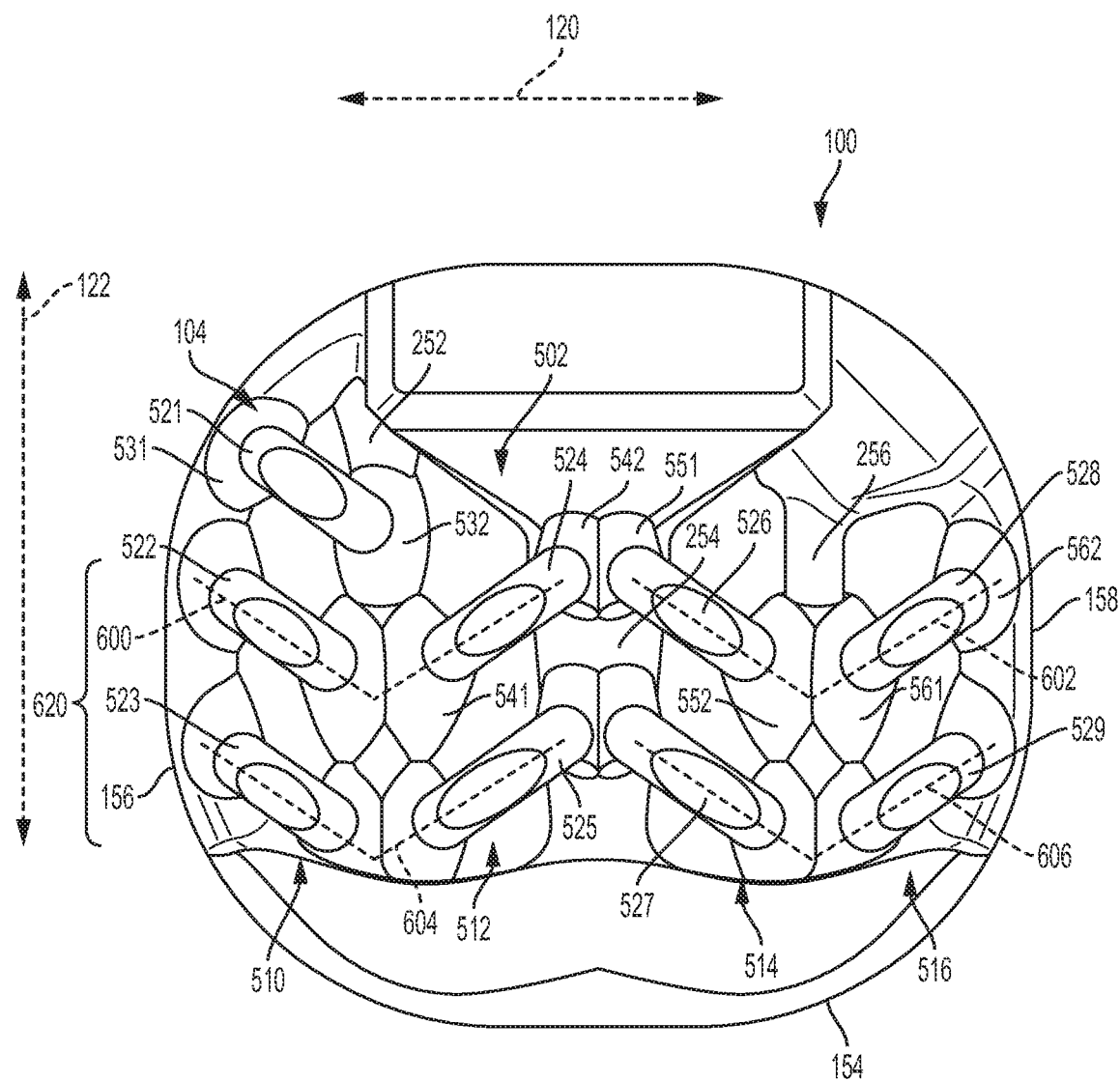
FIG. 10 is a schematic superior view of the implant of FIG. 1.

FIG. 10 is a schematic top view of implant 100. Referring to FIG. 10, plurality of arched bone contacting elements 104 includes a superior set of arched bone contacting elements 502 and an inferior set of arched bone contacting element 504 (visible in FIG. 7). Superior set 502 is further comprised of a first group of arched bone contacting elements 510 (or simply, first group 510), a second group of arched bone contacting elements 512 (or simply second group 512), a third group of arched bone contacting elements 514 (or simply third group 514) and a fourth group of arched bone contacting elements 516 (or simply fourth group 516). In the embodiment of FIG. 10, each group of arched bone contacting elements includes two or more elements that extend between the same two beams or between the same beam and the same side of peripheral structure 150.

As seen in FIG. 10, first group 510 includes first arched bone contacting element 521, second arched bone contacting element 522 and third arched bone contacting element 523.

Each of these elements extend between first lateral side 156 of peripheral structure 150 and first support beam 252. For example, first arched bone contacting element 521 has a flared leg 531 attached to first lateral side 156 and a flared leg 532 attached to first support beam 252. Similarly, each of second arched bone contacting element 522 and third arched bone contacting element 523 have one flared leg attached to first lateral side 156 and another flared leg attached to first support beam 252.

Second group 512 includes fourth arched bone contacting element 524 and fifth arched bone contacting element 525. Each of these elements extend between first support beam 252 and second support beam 254. For example, fourth arched bone contacting element 524 has a flared leg 541 attached to first support beam 252 and another flared leg 542 attached to second support beam 254. Similarly, fifth arched bone contacting element 525 has a flared leg attached to first support beam 252 and another flared leg attached to second support beam 254.

Third group 514 includes sixth arched bone contacting element 526 and seventh arched bone contacting element 527. Each of these elements extend between second support beam 254 and third support beam 256. For example, sixth arched bone contacting element 526 has a flared leg 551 attached to second support beam 254 and another flared leg 552 attached to third support beam 256. Similarly, seventh arched bone contacting element 527 has a flared leg attached to second support beam 254 and another flared leg attached to third support beam 256.

Fourth group 516 includes eighth arched bone contacting element 528 and ninth arched bone contacting element 529. Each of these elements extend between third support beam 256 and second lateral side 158 of peripheral structure 150. For example, eighth arched bone contacting element 528 has a flared leg 561 attached to third support beam 256 and another flared leg 562 attached to second lateral side 158. Similarly, ninth arched bone contacting element 529 has a flared leg attached to third support beam 256 and another flared leg attached to second lateral side 158.

In some cases, some portions of adjacent arched bone contacting elements could be in contact or partially overlap. For example, some embodiments could have flared legs that are in contact or partially overlap. As an example, in FIG. 10, flared leg 532 is disposed adjacent to, and in partial contact with flared leg 541. It may be appreciated, though, that each arched bone contacting element attaches at its ends to portions of the body of implant 100.

Although the ends of two or more arched bone contacting elements may be in contact with one another, the arched portions of each element remain separated from adjacent elements. In other words, there is no intersection between the arched portions of different arched bone contacting elements. Specifically, in some embodiments, the arched portion of each arched bone contacting element may be non-intersecting or separated from one another. Also, there is no intersection of arched bone contacting elements at or near the regions where the arched bone contacting elements contact the vertebrae. Thus it may be seen that implant 100 provides a plurality of arched bone contacting elements 104 that are non-intersecting and are arranged to be in contact with an opposing vertebral surface.

Some embodiments may include provisions that allow a structure to be self-supporting during manufacturing, for example, when the structure is manufactured using a 3D printing process. In some embodiments, the arrangement of arched bone contacting elements may be selected to facilitate self-support during manufacturing (e.g., during a 3D printing process). In some embodiments, the arched bone contacting elements can be arranged in angled orientations relative to the body or an axis of the body. In some embodiments, the arched bone contacting elements may be arranged into a herringbone-like pattern that is further comprised of individual V-like configurations of elements. Such a configuration may enable the implant to be printed with self-supporting structures.

One or more arched bone contacting elements may be angled with respect to one or more axes of an implant. Referring to FIG. 10, for example, second arched bone contacting element 522 is oriented at an oblique angle with respect to lateral axis 120 (and also with respect to posterior-anterior axis 122). Additionally, fourth arched bone contacting element 524 is oriented at an oblique angle with respect to lateral axis 120 (and also with respect to posterior-anterior axis 122). Moreover, second bone contacting element 522 and fourth bone contacting element 524 are oriented at different angles from lateral axis 122. As shown in FIG. 10, the remaining arched bone contacting elements may also be oriented at an oblique angle with respect to lateral axis 120 of implant 100. Thus it may be seen that the arched bone contacting elements are not arranged in parallel on implant 100.

In some embodiments, at least two arched bone contacting elements may be arranged in a V-like configuration, or pattern, on a body of an implant. For example, second arched bone contacting element 522 and fourth arched bone contacting element 524 are arranged in a first V-like configuration 600. Additionally, sixth arched bone contacting element 526 and eighth arched bone contacting element 528 are arranged in a second V-like configuration 602. Also, third arched bone contacting element 523 and fifth arched bone contacting element 525 are arranged in a third V-like configuration 604. Finally, seventh arched bone contacting element 527 and ninth arched bone contacting element 529 are arranged in a fourth V-like configuration 606. Although the present embodiment includes four V-like configurations on the superior side (i.e., superior set of arched bone contacting elements 502), as well as another four V-like configurations on the inferior side, other embodiments could include any other number of V-like configurations on the superior side or the inferior side.

In different embodiments, the positioning and orientation of V-like configurations could vary. In some embodiments, all of the V-like configurations may be oriented in a similar direction. In other embodiments, two or more V-like configurations could be oriented in different directions. Moreover, in some cases, two or more V-like configurations could be arranged in rows and/or columns.

In the embodiment shown in FIG. 10, each V-like configuration has a common orientation corresponding to the posterior-anterior axis 122. Specifically, each configuration is arranged such that the tip of the V points along posterior-anterior axis 122 and in the direction towards posterior side 154. Moreover, first V-like configuration 600 and second V-like configuration 602 are disposed adjacent to one another in a first row such that they have different positions along lateral axis 120. Likewise, third V-like configuration 604 and fourth V-like configuration 606 are disposed adjacent to one another in a second row. Furthermore, first V-like configuration 600 and third V-like configuration 604 are disposed adjacent to one another in a first column such that they have different positions along posterior-anterior axis 122. Likewise, second V-like configuration 602 and fourth V-like configuration 606 are disposed adjacent one another in a second column. As seen in FIG. 10, when considered together, the four V-like configurations form a larger herringbone pattern 620 on body 102.

Each V-like configuration may be centered around a single support beam. For example, first V-like configuration 600 and second V-like configuration may be centered around first support beam 252. Also, third V-like configuration and fourth V-like configuration may be centered around third support beam 256.

Each V-like configuration may extend from a lateral side of body 102 to a central support beam (e.g., second support beam 254). For example, first V-like configuration 600 extends from first lateral side 156 to second support beam 254. And second V-like configuration 602 extends from second support beam 254 to second lateral side 158.

In some cases, orienting arched bone contacting elements into a herringbone pattern may facilitate easier insertion of the implant. In particular, by angling the arched bone contacting elements away from the lateral direction, the elements may present a smaller surface area along the implantation direction (i.e., the posterior direction), which could potentially ease insertion effort.

The arrangement of arched bone contacting elements may also be designed to achieve a desired total open volume. As used herein a total volume is the combined volume of any openings between arched bone contacting elements, any openings in the body, or between arched bone contacting elements and the body. This open configuration may facilitate bone growth in and through the implant. A portion or all of the open spaces is optionally filled with a bone graft or bone growth promoting material prior to or after insertion of the implant to facilitate bone growth.

The total volume of the open spaces (also referred to simply as the open space volume) within any particular implant is dependent on the overall dimension of the implant as well as the size and dimension of individual components within the implant including arched bone contacting elements. The open space volume may range from about 20% to 80% of the volume of the implant. In some embodiments, implant 100 may have an open space volume that is between 25% and 80% of the implant's total volume. In still further embodiments, implant 100 may have an open space volume that is between 50% and 70% of the total implant volume.

In some embodiments, an implant can be configured with one or more symmetries. In some cases, an implant may have a mirrored symmetry about one or more reference planes. In other cases, an implant may have a translational symmetry about one or more reference planes. In still other cases, an implant could have both a mirror symmetry and a translational symmetry.

Referring to FIGS. 1 and 2, implant 100 may include at least one mirror symmetry. For purposes of reference, implant 100 may be split into a superior half and an inferior half. Here, the "superior half" of implant 100 includes the portions of body 102 and plurality of arched bone contacting elements 104 disposed above the transverse plane. Likewise, the "inferior half" of implant 100 includes the portions of body 102 and plurality of arched bone contacting elements 104 disposed below the transverse.

With respect to the transverse plane (which coincides generally with body 102 in this embodiment), it may be seen that the superior half of implant 100 mirrors the inferior half of implant 100. This includes not only the geometry of the body but also the shape, size and orientations of each arched bone contacting element. It may be appreciated that this mirror symmetry may only be approximate in some embodiments. The symmetric configuration of implant 100, for example the mirror symmetry between the superior and inferior halves of implant 100, may help to balance loads in the vertical direction, or the direction along the length of the spine.

Additional Embodiments

In different embodiments, the dimensions of an implant can vary. Exemplary dimensions that could be varied include length, width and thickness. Moreover, in some cases, the diameter of one or more arched bone contacting elements could vary from one embodiment to another.

Figure 11:
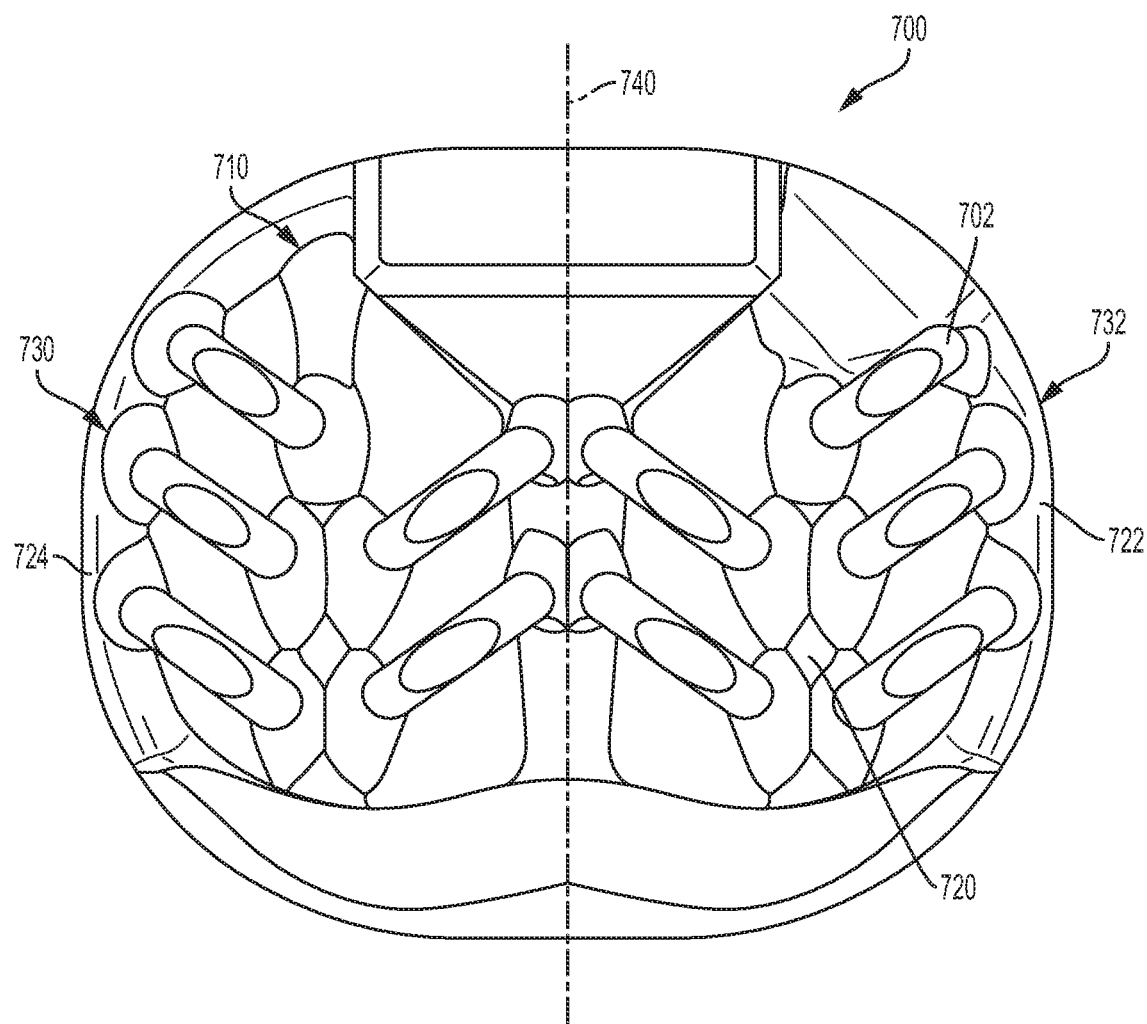
FIG. 11 is a schematic superior view of another embodiment of an implant.

FIG. 11 is a schematic view of another embodiment of an implant 700. Implant 700 may be similar in many ways to implant 100 discussed above and shown in FIGS. 1-10. In some embodiments, implant 700 may have a greater width and length (and thus a larger overall footprint) than implant 100. In order to accommodate the larger size, implant 700 may include an additional arched bone contacting element 702 on superior side 710, as well as a corresponding element on an inferior side (not shown).

As seen in FIG. 11, arched bone contacting element 702 extends from support beam 720 to lateral side 722 of implant 700. With this additional arched bone contacting element, group of arched bone contacting elements 730 on lateral side 724 is seen to have the same number of elements (i.e., three) as group of arched bone contacting elements 732 on lateral side 722. This configuration of arched bone contacting elements is thus seen to have a mirror symmetry about a central axis 740 of implant 700.

Figure 12:
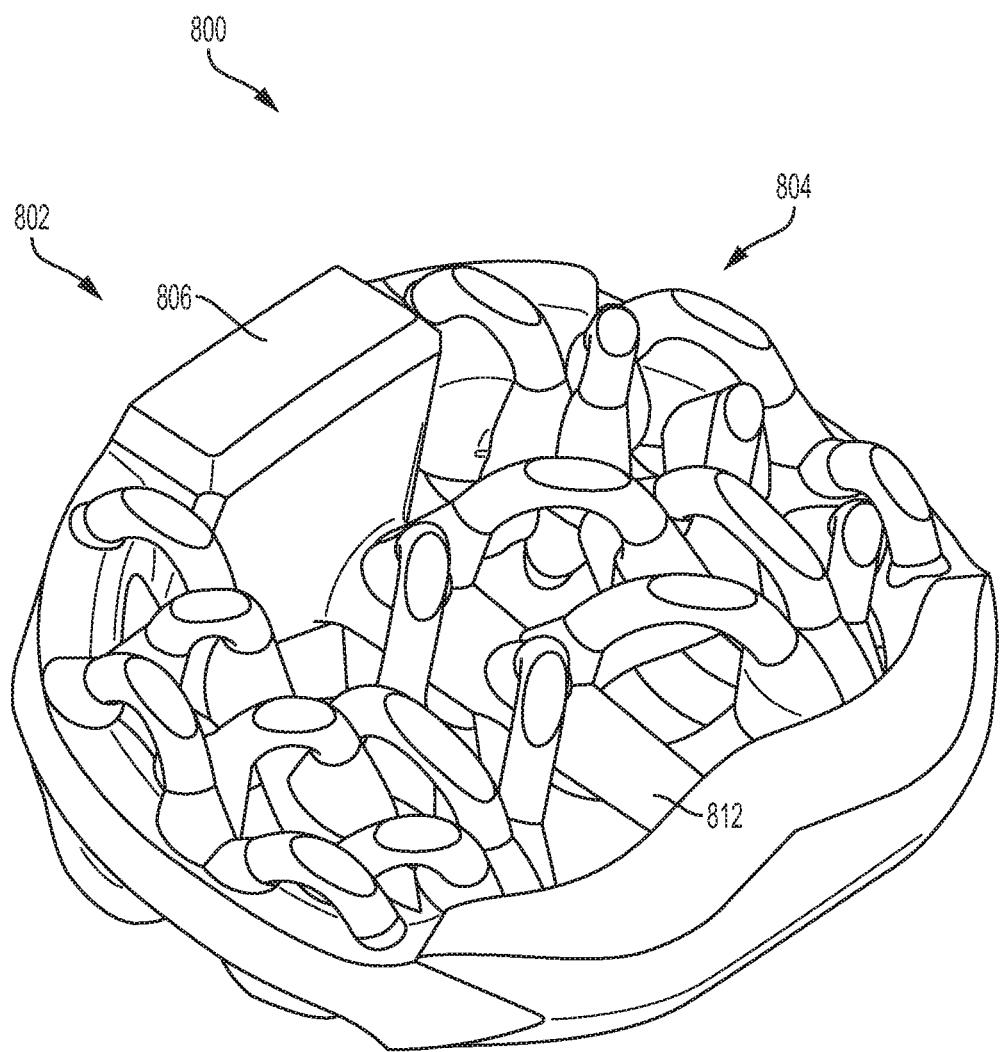
FIG. 12 is a schematic isometric view of another embodiment of an implant.
Figure 13:
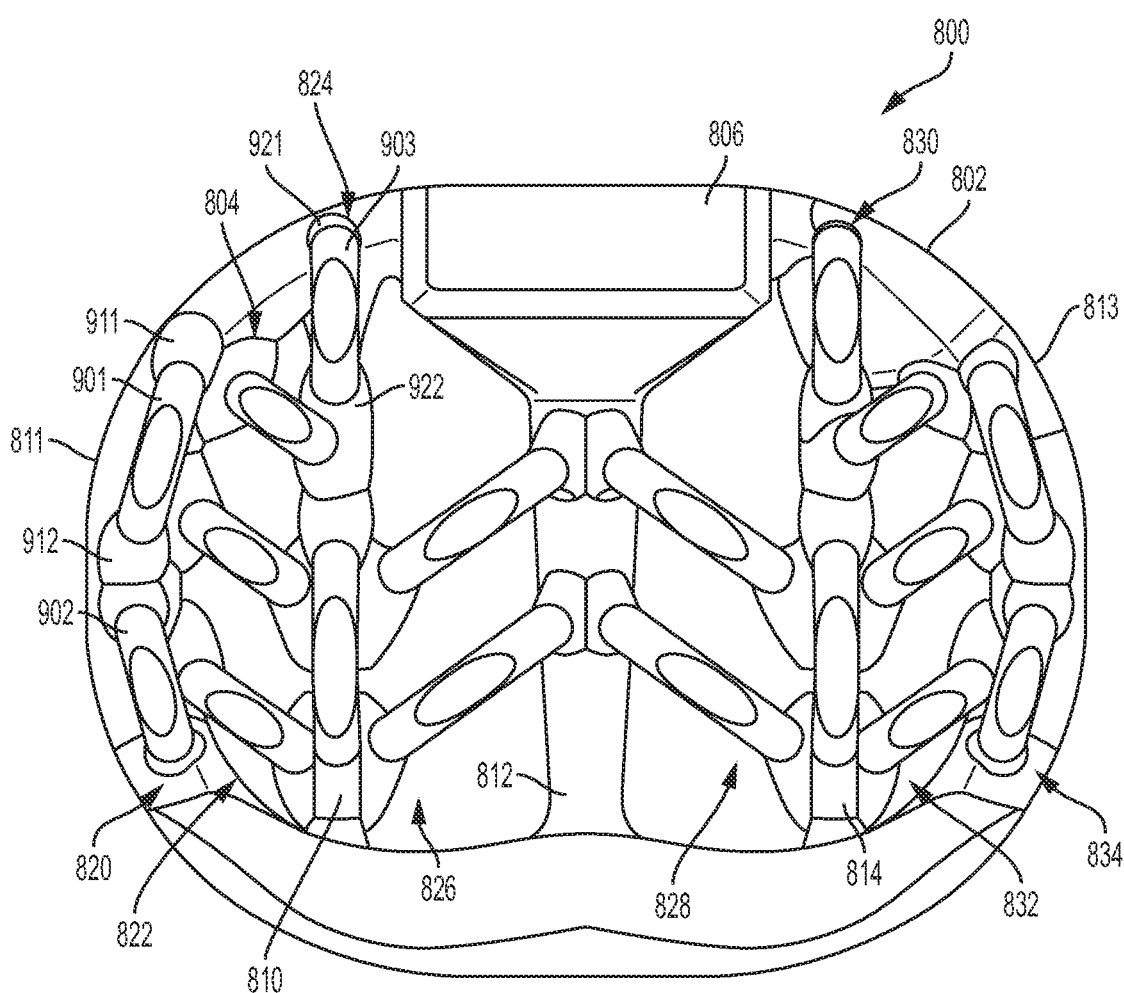
FIG. 13 is a schematic superior view of the implant of FIG. 12.

FIGS. 12-13 illustrate a schematic view of another embodiment of an implant 800. Implant 800 may be similar in many ways to implant 100 and implant 700 discussed above and shown in FIGS. 1-11. In some embodiments, implant 800 may have a greater width and length (and thus a larger overall footprint) than implant 700.

Some embodiments can include one or more arched bone contacting elements that are attached at both ends to a single support beam. Some embodiments can include one or more arched bone contacting elements that are attached to a single segment of a peripheral structure.

Referring to FIGS. 12-13, implant 800 is comprised of a plurality of arched bone contacting elements 804 attached to a body 802. Body 802 is further comprised of a peripheral structure 806, a first support beam 810, a second support beam 812 and a third support beam 814.

Referring now to FIG. 13, plurality of arched bone contacting elements 804 is further comprised of a first group of arched bone contacting elements 820 (or first group 820), a second group of arched bone contacting elements 822 (or second group 822), a third group of arched bone contacting elements 824 (or third group 824), a fourth group of arched bone contacting elements 826 (or fourth group 826), a fifth group of arched bone contacting elements 828 (or fifth group 828), a sixth group of arched bone contacting elements 830 (or sixth group 830), a seventh group of arched bone contacting elements 832 (or seventh group 832) and an eighth group of arched bone contacting elements 834 (or eighth group 834).

Second group 822 includes arched bone contacting elements extending from first lateral side 811 of peripheral structure 806 to first support beam 810. Fourth group 826 includes arched bone contacting elements extending from first support beam 810 to second support beam 812. Fifth group 828 includes arched bone contacting elements extending from second support beam 812 to third support beam 814. Seventh group 832 includes arched bone contacting elements extending from third support beam 814 to second lateral side 813 of peripheral structure 806. Moreover, the arched bone contacting elements in second group 822, fourth group 826, fifth group 828 and seventh group 832 are generally arranged into V-like configurations organized into a herringbone-like pattern, similar to the arrangement of arched bone contacting elements of implant 100.

As implant 800 has an increased footprint compared to implant 100 and implant 700, additional arched bone contacting elements may be included to provide a larger (partial) contact surface on the superior and inferior sides of implant 800. In the embodiment shown in FIGS. 12-13, some of these additional arched bone contacting elements are added along the lateral sides of body 802 as well as first support beam 810, second support beam 812 and third support beam 814.

First group 820 includes an arched bone contacting element 901 and an arched bone contacting element 902, which are both connected at each end to first lateral side 811 of peripheral structure 806. Specifically, for example, arched bone contacting element 901 includes a first flared leg 911 attached to first lateral side 811 and a second flared leg 912 attached to first lateral side 811.

Additionally, third group 824 includes three arched bone contacting elements, each of which are attached at both ends to first support beam 810. For example, arched bone contacting element 903 includes first flared leg 921 attached to first support beam 810 and a second flared leg 922 attached to first support beam 810. Likewise, sixth group 830 includes three arched bone contacting elements. Each of these elements includes two flared legs that are both attached at third support beam 814. Additionally, eighth group 834 includes two arched bone contacting elements. Each of these elements includes two flared legs that are both attached at second lateral side 813 of peripheral structure 806.

Surface Texturing

Embodiments can include provisions for texturing one or more surfaces of an implant. Such texturing can increase or otherwise promote bone growth and/or fusion to surfaces of the implant. In some embodiments, arched bone contacting elements and/or sections of a body may be textured.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. In some embodiments, the roughness can be created by 3D printing a raised pattern on the surface of one or more regions of an implant. In some embodiments, the resulting roughened surface may have pores of varying sizes. In some embodiments, pore sizes could range between approximately 0.2 mm and 0.8 mm. In one embodiment, pore sizes could be approximately 0.5 mm. Of course in other embodiments, surface roughness comprising pore sizes less than 0.2 mm and/or greater than 0.8 mm are possible.

Figure 15:
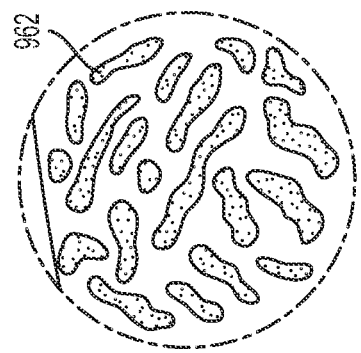
FIG. 15 is a schematic view of a roughened surface region, according to an embodiment.
Figure 14:
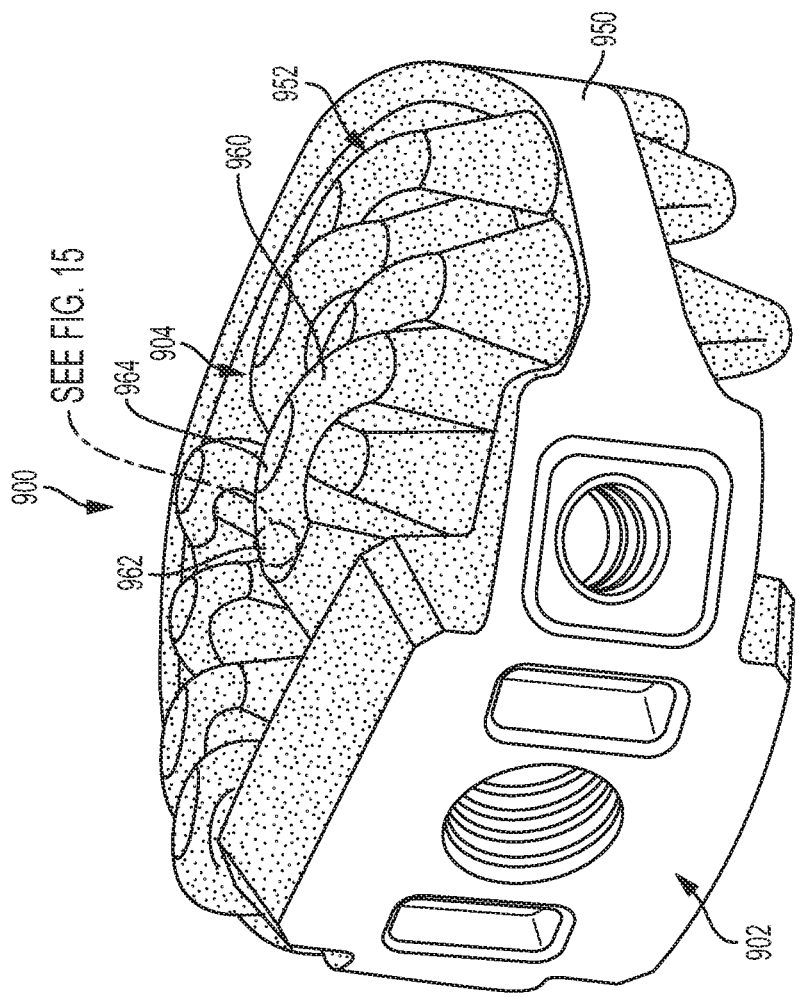
FIG. 14 is a schematic isometric view of an embodiment of an implant including a roughened surface.

An embodiment using textured surfaces is shown in an isometric view of an alternative embodiment and implant 900 seen in FIG. 14. As seen in FIG. 14, implant 900 includes a smooth peripheral surface 902. The remaining surfaces of implant 900, however, have been roughened. These include the visible portions of superior surface 904, which is further comprised of superior surfaces of peripheral structure 950 and the surfaces of plurality of arched bone contacting elements 952. For purposes of illustration, the roughened surfaces are indicated schematically using stippling. These roughened or porous surfaces may help improve bone growth along surfaces of the implant. As a particular example, arched bone contacting element 960 is seen to have a roughened surface region 962 (also seen in the enlarged schematic view of FIG. 15) that extends through the entire element including distal surface region 964 which is intended to directly contact an adjacent vertebra.

It may be appreciated that any of the embodiments illustrated in the Figures can include one or more roughened surfaces. For example, in some embodiments implant 100, implant 700 or implant 900 could include one or more roughened surfaces. Moreover, the roughened surfaces could be selectively applied to some portions of an implant but not others.

Bone Growth Promoting Material

In some embodiments, bone growth can be facilitated by applying a bone growth promoting material in or around portions of an implant. As used herein, a "bone growth promoting material" (or BGPM) is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant.

Manufacturing and Materials

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, Ti6-Al4-V ELI (ASTM F 136), or Ti6-Al4-V (ASTM F 1108 and ASTM F 1472)) and inert, biocompatible polymers, such as polyether ether ketone (PEEK) (e.g. PEEK-OPTIMA®, Invibio Inc). Optionally, the implant contains a radiopaque marker to facilitate visualization during imaging.

In different embodiments, processes for making an implant can vary. In some embodiments, the entire implant may be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material and their combinations. Moreover, the embodiments can make use of any of the features, parts, assemblies, processes and/or methods disclosed in the "Coiled Implants Application".

The design of the embodiments (e.g., implant 100, implant 700 and implant 900) may help provide improved and/or accelerated bone fusion. Specifically, following implantation of one of the exemplary implants, bone fusion may first occur at one or more distal surfaces, or apexes, of the arched bone contacting elements. From these distal surfaces bone growth may continue down along the arched portions of each arched bone contacting element and may therefore be directed to grow towards an interior of the implant. Thus new bone growth initiated at the distal surfaces on the superior and inferior sides of the implant may be directed towards the center of the implant and may eventually meet to form continuous sections of new bone growth that extend from one vertebral body, through the implant and then to the adjacent vertebral body. Moreover, this may result in an accelerated fusion process between vertebral bodies over configurations where bone contacting elements are primarily disposed on the implant surface and do not extend inwardly.

Implant for Oblique Lumbar Interbody Fusion

Figure 16:
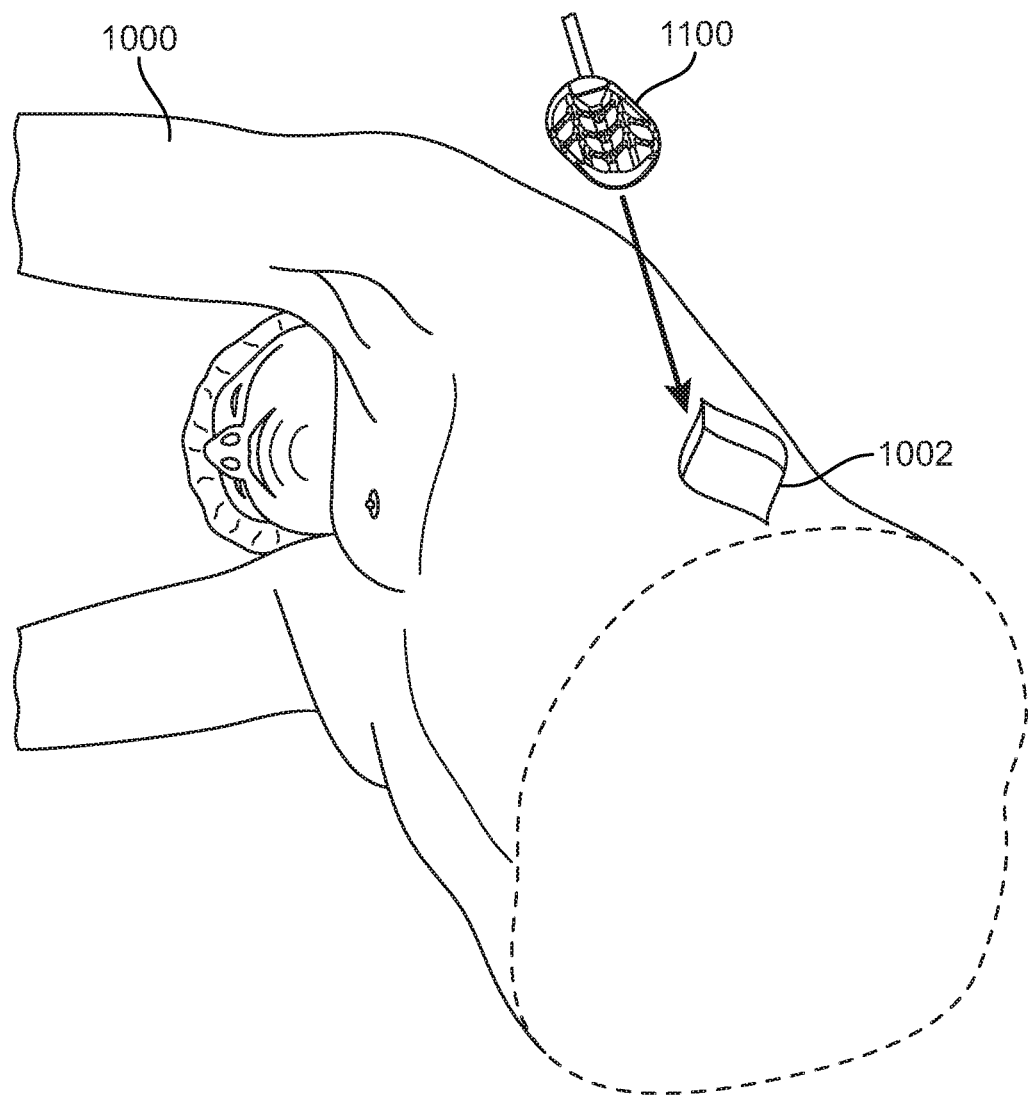
FIG. 16 is a schematic view of a patient undergoing and oblique lateral interbody fusion procedure, according to an embodiment.

FIGS. 16-24 illustrate various schematic views of another embodiment of an implant as well as methods of use. In some embodiments, an implant may be inserted using an oblique lumbar interbody fusion (OLIF) surgical procedure, where the disc space is fused by approaching the spine from the side. FIG. 16 illustrates a schematic view of a patient 1000 lying on his side with an implant 1100 positioned for insertion into his body. In the OLIF approach, an incision 1002 (which may be 3 to 5 inches in length in some cases) may be made on the side of the abdomen.

Figure 17:
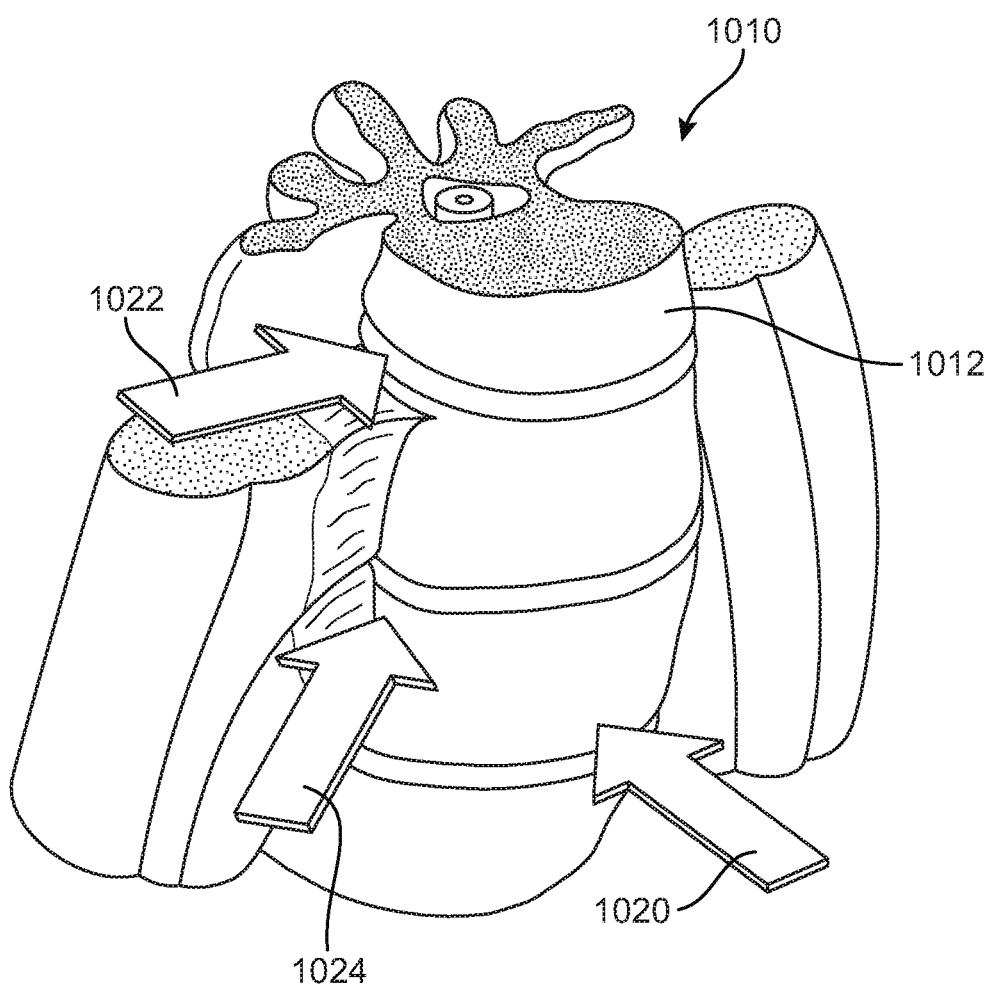
FIG. 17 is a schematic view of a portion of a spine, according to an embodiment.

FIG. 17 illustrates a schematic view of a region of spine 1010, including a plurality of vertebrae 1012. For purposes of understanding the OLIF surgical procedure, several variations on spinal procedures are shown. These procedures are schematically represented in FIG. 17 by the direction of their approach to the spine. They include anterior lumbar interbody fusion (ALIF) approach 1020, direct lateral interbody fusion (DLIF) approach 1022 and OLIF approach 1024. In ALIF approach 1020, a surgical cut is made at the front of the abdomen and an implant is inserted along a posterior-anterior direction with respect to the spine. In DLIF approach 1022, a surgical cut is made on the side of the abdomen and an implant is inserted along a lateral direction with respect to the spine. OLIF approach 1024 may be similar to DLIF approach 1022 in some respects. However, in contrast to DLIF approach 1022, in OLIF approach 1024, the implant is inserted from an oblique angle, thereby allowing more direct access to the last lumbar vertebra which would be obscured by the pelvic bone in a direct lateral approach.

Figure 18:
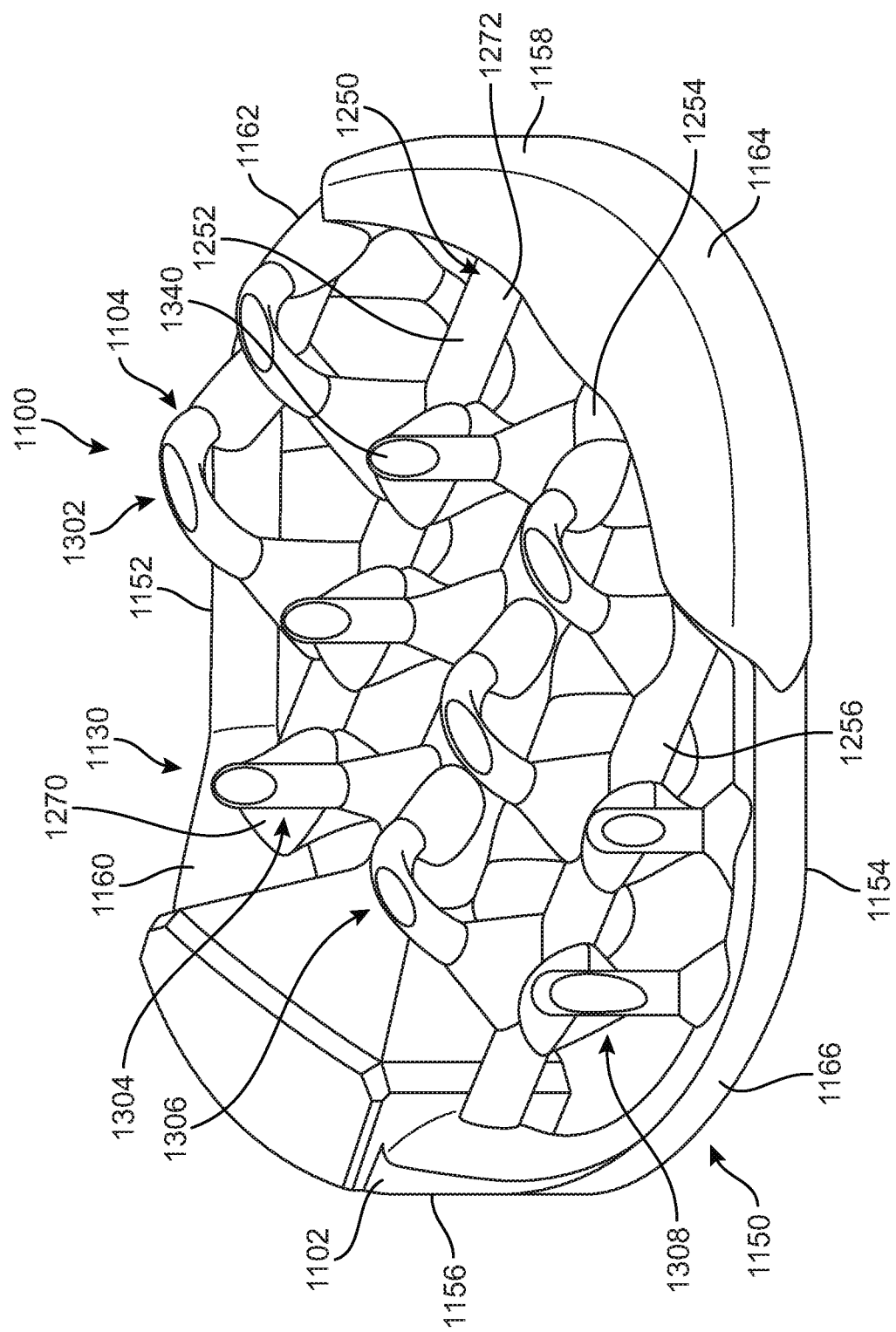
FIG. 18 is a schematic isometric view of an embodiment of an implant, according to an embodiment.
Figure 19:
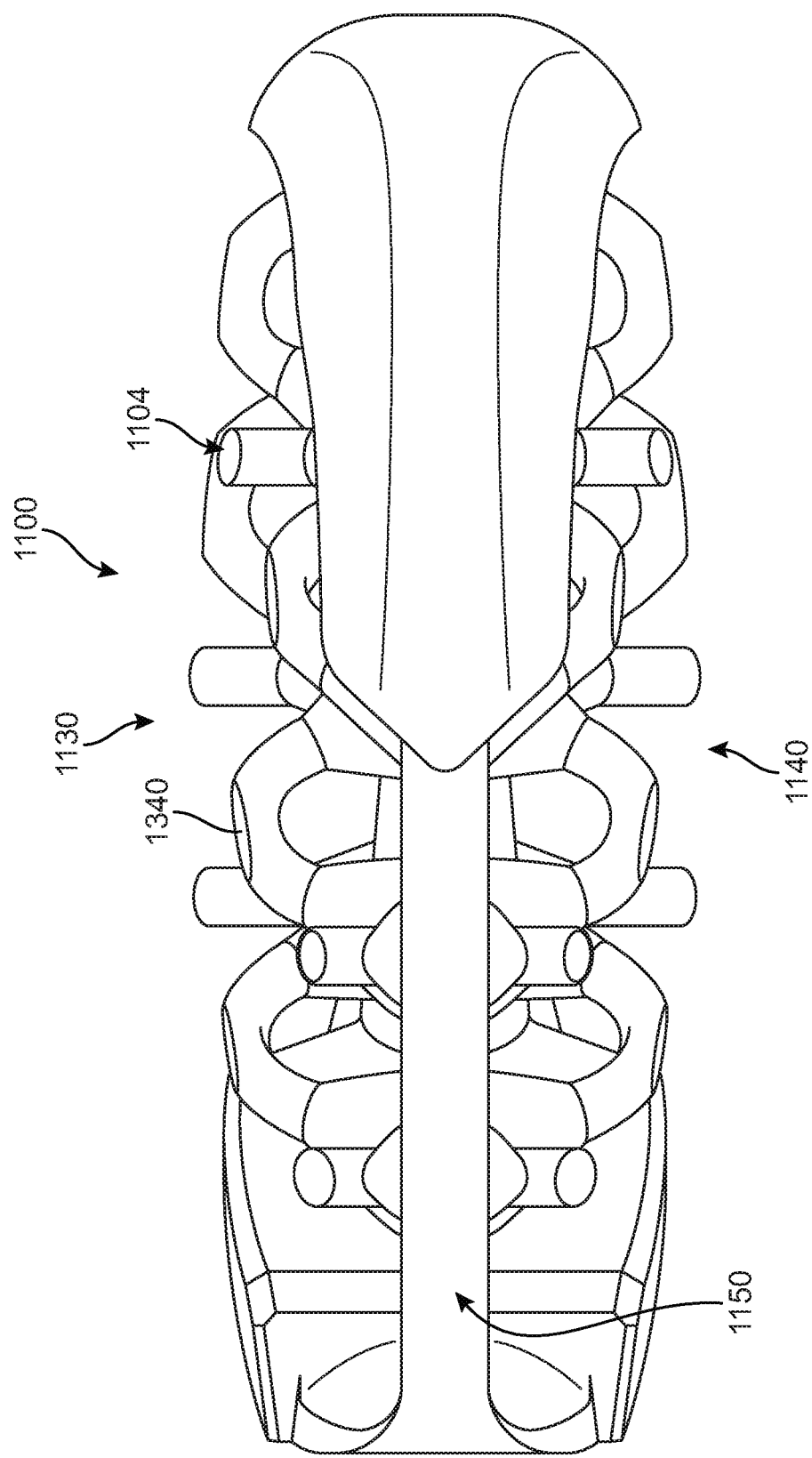
FIG. 19 is a schematic view of an embodiment of the implant of FIG. 16.

FIGS. 18-19 illustrate an isometric view and a side view, respectively, of an embodiment of OLIF implant 1100, also referred to simply as implant 1100. Implant 1100 may also be referred to as a cage or fusion device. In some embodiments, implant 1100 is configured to be implanted within a portion of the human body. In some embodiments, implant 1100 may be configured for implantation into the spine. In some embodiments, implant 1100 may be a spinal fusion implant, or spinal fusion device, that is inserted between adjacent vertebrae to provide support and/or facilitate fusion between the vertebrae.

In some embodiments, implant 1100 may include a body 1102. Body 1102 may generally provide a frame or skeleton for implant 1100. In some embodiments, implant 1100 may also include a plurality of bone contacting elements 1104. Plurality of bone contacting elements 1104 may be attached, and/or continuously formed (or "integrally formed") with, body 1102.

In FIGS. 18-19, implant 1100 is understood to be configured with an anterior side and a posterior side. Implant 1100 may also include a first lateral side and a second lateral side that extend between the posterior side and the anterior side on opposing sides of implant 1100. Furthermore, implant 1100 may also include a superior side 1130 and an inferior side 1140 (see FIG. 19).

For purposes of clarity, the discussion primarily focusses on superior side 1130 of implant 1100. However, it may be appreciated that in some cases implant 1100 is symmetric about the transverse plane that divides implant 1100 into superior side 1130 and inferior side 1140. In such cases, inferior side 1140 may include identical provisions to those discussed for superior side 1130.

In some embodiments, a body may comprise a peripheral structure and one or more support beams that extend from the peripheral structure. A peripheral structure may be comprised of any number of plates, walls or similar structures. In some embodiments, the peripheral structure could comprise a ring. In other words, in some embodiments, the peripheral structure could be a peripheral ring structure. As seen in FIGS. 18-19, body 1102 may be further comprised of a peripheral structure 1150. Peripheral structure 1150 is seen to have a rectangular ring geometry.

Referring to FIG. 18, peripheral structure 1150 may be further comprised of an anterior side 1152, a posterior side 1154, a first lateral side 1156 and a second lateral side 1158. As seen in FIG. 18, in this exemplary embodiment, peripheral structure 1150 is a continuous structure so that anterior side 1152 is connected to first lateral side 1156. Also, first lateral side 1156 is connected to posterior side 1154. Also, posterior side 1154 is connected to second lateral side 1158. And second lateral side 1158 is connected to anterior side 1152. That is, anterior side 1152, first lateral side 1156, posterior side 1154 and second lateral side 1158 together form a continuous or unbroken rectangular ring.

Peripheral structure 1150 may also be characterized by four corner portions. These include a first corner portion 1160, a second corner portion 1162, a third corner portion 1164, and a fourth corner portion 1166. First corner portion 1160 may be disposed at the intersection of anterior side 1152 and first lateral side 1156. Second corner portion 1162 may be disposed at the intersection of anterior side 1152 and second lateral side 1158. Third corner portion 1164 may be disposed at the intersection of posterior side 1154 and second lateral side 1158. And fourth corner portion 1166 may be disposed at the intersection of posterior side 1154 and first lateral side 1156.

In the exemplary embodiment of FIG. 18, first corner portion 1160 and third corner portion 1164 have an increased thickness compared to second corner portion 1162 and fourth corner portion 1166. Moreover, as discussed in further detail below, fastener and/or insertion tool receiving provisions may be disposed in first corner portion 1160. These provisions may help facilitate insertion of implant 1100 along an oblique angle.

In some embodiments, a body may be provided with one or more support beams (or support structures) that act to reinforce a peripheral structure. In some embodiments, one or more support beams could be disposed along the interior of a peripheral structure. For example, in some embodiments, one or more support beams could extend from a first location on an inwardly (or proximally) facing surface of the support structure to a second location on the inwardly facing surface of the support structure. In other words, in some embodiments, one or more support beams may span an interior region bounded by the peripheral structure.

As seen in FIG. 18, body 1102 includes a plurality of support beams 1250. These include first support beam 1252, second support beam 1254 and third support beam 1256. In the embodiment shown in FIG. 18, each of these support beams extends from a first location on inwardly facing surface of peripheral structure 1150 to a second location on the inwardly facing surface of peripheral structure 1150.

Referring to FIG. 18, first support beam 1252 includes a first end 1270 attached to a first location of peripheral structure 1150 and a second end 1272 attached at a second location of peripheral structure 1150. Likewise, each of second support beam 1254 and third support beam 1256 include opposing ends attached to different locations along peripheral structure 1150. With this arrangement, plurality of support beams 1250 are seen to span an interior region (or central region) of implant 1100 that is bounded by peripheral structure 1150.

The plurality of support beams 1250 may be characterized as being centrally located within implant 1100 with respect to peripheral structure 1150. As used herein, "centrally located" does not refer to a precise location that is at the geometric center or center of mass of an implant, but rather a general area or region disposed inwardly of a peripheral structure (e.g., within the interior region). Thus, in the following description and in the claims, a support beam may be referred to as a central beam.

In different embodiments, the number of support beams could vary. In some embodiments, a single support beam could be used. In other embodiments, two or more support beams could be used. In the exemplary embodiment shown in FIG. 18, three support beams are used.

In different embodiments, the geometry of one or more support beams could vary. In some embodiments, one or more support beams could have a curved geometry. In other embodiments, one or more support beams could have a substantially straight geometry. In the embodiment shown in FIG. 18, each of plurality of support beams 1250 has a substantially straight geometry. Moreover, the cross-sectional geometry of each support beam is substantially rounded. However, in other embodiments, one or more support beams could have any other cross-sectional shape, including but not limited to: rectangular shapes, polygonal shapes, regular shapes and/or irregular shapes.

In different embodiments, the thickness of one or more support beams could vary. Generally, the thickness (or diameter) of a support beam could vary in a range between 1% and 95% of the width (or length) of an implant.

In at least some embodiments, support beams in the body of an implant may be coplanar. In FIG. 18, first support beam 1252, second support beam 1254 and third support beam 1256 are seen to reside in a similar plane of implant 1100. The coplanar arrangement of support beams may help provide a generally symmetric arrangement for implant 1100 between the superior and inferior sides.

Generally, the geometry of one or more portions of the body of an implant could vary from one embodiment to another. For example, portions of a body can include one or more windows, slots and/or openings that may facilitate bone growth through the implant and/or may reduce weight.

Some embodiments can include one or more fastener receiving provisions. In some embodiments, an implant can include one or more threaded cavities. In some embodiments, a threaded cavity can be configured to mate with a corresponding threaded tip on an implantation tool or device. In other embodiments, a threaded cavity can receive a fastener for purposes of fastening an implant to another device or component in an implantation system that uses multiple implants and/or multiple components.

Figure 20:
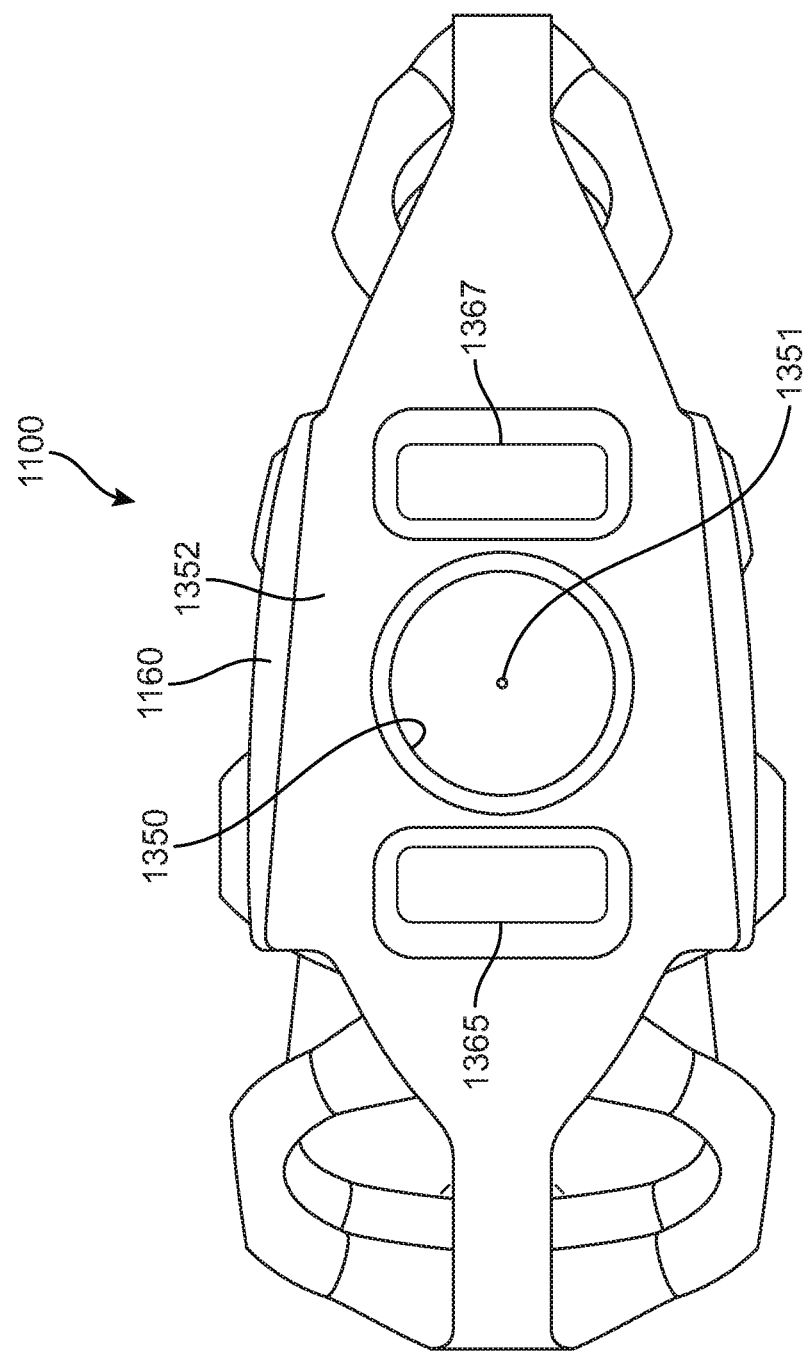
FIG. 20 is a schematic view of an embodiment of the implant of FIG. 16, in which a threaded cavity is visible.

As best seen in FIG. 20, implant 1100 includes a receiving portion 1352 disposed at first corner portion 1160. Receiving portion 1352 further includes threaded cavity 1350. In some embodiments, threaded cavity 1350 may receive the threaded tip of an implantation tool (not shown). Such a tool could be used to drive implant 1100 between adjacent vertebral bodies. Optionally, in some cases, implant 1100 may also include a pair of indentations (indentation 1365 and indentation 1367) that may facilitate alignment between an implantation tool and implant 1100. In some embodiments, threaded cavity 1350 could be used to fasten implant 1100 to a separate component (not shown) of a broader implantation system.

In some embodiments, a bone contacting element may include a first end portion, an intermediate portion and a second end portion. In some embodiments, the intermediate portion may have a curved geometry. In some embodiments, the first end portion and/or the second end portion could have a flared geometry. In such cases, an end having a flared geometry may be referred to as a "flared leg" of the bone contacting element.

Figure 21:
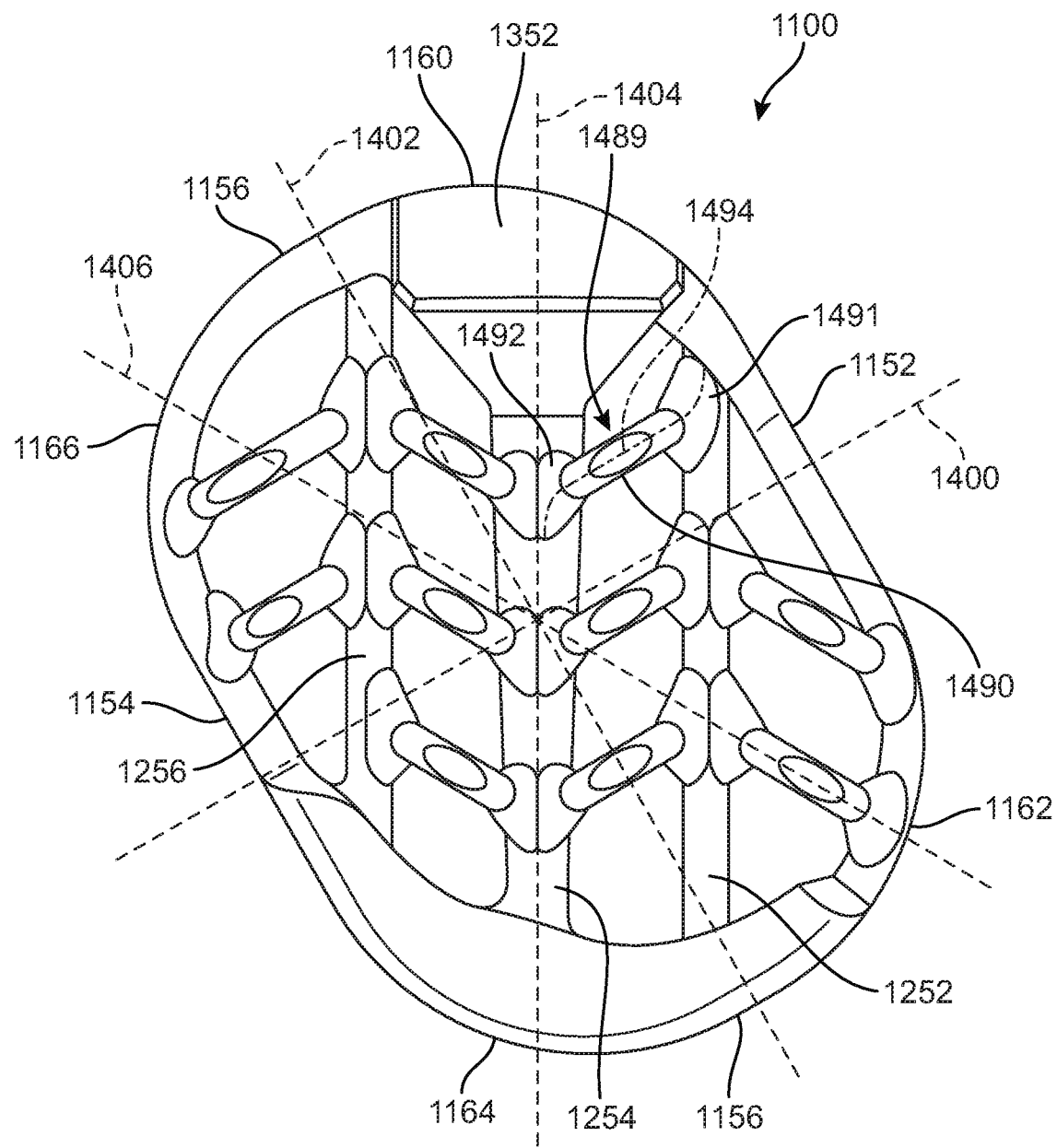
FIG. 21 is a schematic view of an embodiment of the implant of FIG. 16.

In different embodiments, the geometry of a bone contacting element could vary. In some embodiments, bone contacting elements could have spiraling or helical geometries. In other embodiments, bone contacting elements could have other curved geometries. An exemplary geometry for a bone contacting element is depicted in FIG. 21. As seen in FIG. 21, implant 1100 includes a bone contacting element 1489 that is further comprised of a first end portion 1491, a second end portion 1492 and an intermediate portion 1490. The curvature of bone contacting element 1489 is represented by curve 1494 that extends along the length of bone contacting element 1489. It may be seen from FIG. 21 that curve 1494 is not straight or planar and instead curves from first end portion 1491 to second end portion 1492. In some cases, curve 1494 may be slightly helical. Similarly, in some embodiments, the remaining bone contacting elements may have similarly curved geometries.

As seen in FIGS. 18-19, implant 1100 includes a plurality of bone contacting elements 1104. Each bone contacting member may include any of the features described above for the bone contacting elements shown in FIGS. 8-10. In some embodiments, bone contacting elements 1104 may be grouped into various rows or sets. As seen in FIG. 18, these may include first set 1302, second set 1304, third set 1306 and fourth set 1308. In this case, first set 1302 includes two elements extending from peripheral structure 1150 to first support beam 1252. Likewise, second set 1304 includes three elements extending from first support beam 1252 to second support beam 1254. In addition, third set 1306 includes three elements extending from second support beam 1254 to third support beam 1256. Finally, fourth set 1308 includes two elements extending from third support beam 1256 to peripheral structure 1150.

In some embodiments, bone contacting elements within each group may share some properties. For example, in the exemplary embodiment of FIG. 18, bone contacting elements in each group may have a similar orientation. In some cases, bone contacting elements in each group may have an approximately similar size (e.g., height and/or length), especially relative to sizes of elements on other groups. In other embodiments, arched bone contacting elements within a group could have different orientations and/or sizes.

In some embodiments, a bone contacting element can include provisions for engaging a vertebral body following implantation. In some embodiments, one or more bone contacting elements can include at least one bone contacting region. As previously discussed, bone contacting regions may be regions of the surface of a bone contacting member where the curvature varies compared to surrounding areas. Specifically, the surface within the bone contacting region could be convex, concave and/or approximately flat to provide a better fit with vertebral endplates upon implantation. In FIGS. 18-19, plurality of bone contacting elements 1104 are seen to include bone contacting regions 1340. Together, these bone contacting regions provide a partial smooth surface that can engage a vertebral body.

Embodiments could include any number of bone contacting elements. Some embodiments may include a single bone contacting element. Still other embodiments could include any number of bone contacting elements in the range between 2 and 50. In still further embodiments, an implant could include more than 50 elements. In the exemplary embodiment shown in FIG. 18, implant 1100 includes 20 bone contacting elements, including ten elements on superior side 1130 and ten elements on inferior side 1140. Specifically, first set 1302 includes two elements, second set 1304 includes three elements, third set 1306 includes three elements and fourth set 1308 includes two elements. The number of bone contacting elements used can vary according to factors including implant size, desired implant strength, desired volume for bone graft or other bone growth promoting materials as well as possibly other factors.

In different embodiments, the arrangement of bone contacting elements in an implant could vary. In some embodiments, bone contacting elements could attach to any portions of a peripheral structure, to any beams of an implant, as well as other bone contacting elements. In some embodiments, a bone contacting element could extend across the entire width of an implant. In other embodiments, a bone contacting element may only extend across a portion of the width of an implant.

In some embodiments, pairs of bone contacting elements could be arranged into V-like configurations that collectively form a herringbone pattern, such as one of the patterns discussed above and shown in FIGS. 10-13. Alternatively, in other embodiments, bone contacting elements could be arranged in any other pattern or configuration.

Embodiments can include provisions to facilitate the oblique lateral insertion of an implant. In some embodiments, one or more features of an implant may be aligned with an insertion axis.

FIG. 21 is a schematic view of an embodiment of implant 1100. Referring to FIG. 21, implant 1100 may be characterized by multiple axes. Implant 1100 may be associated with a posterior-anterior axis 1400 that extends from anterior side 1152 to posterior side 1154. In addition, implant 1100 may be associated with a lateral axis 1402 that extends from first lateral side 1156 to second lateral side 1158.

Implant 1100 may further be associated with additional axes that are oriented at oblique angles with respect to anterior-posterior axis 1400 and lateral axis 1402. As seen in FIG. 21, implant 1100 may include a first diagonal axis, also referred to as insertion axis 1404. Insertion axis 1404 may extend between first corner portion 1160 and third corner portion 1164. In some cases, insertion axis 1404 may run in parallel with one or more of support beams 1250. Implant 1100 may also include a second diagonal axis 1406, which extends from second corner portion 1162 to fourth corner portion 1166.

As seen in FIG. 21, receiving portion 1352 may be associated with insertion axis 1404. More specifically, threaded cavity 1350 may have a central axis 1351 (see FIG. 20) that is parallel with insertion axis 1404. This configuration ensures that implant 1100 can be inserted at an oblique angle to the spine while ensuring that implant 1100 is correctly oriented with respect to the anterior-posterior and lateral directions post-insertion.

In different embodiments, the orientation of one or more beams could vary. In some embodiments, two or more support beams could be oriented in parallel. In other embodiments, two or more support beams could be disposed at oblique angles to one another. In the exemplary embodiment, first support beam 1252, second support beam 1254 and third support beam 1256 may be disposed in parallel to one another. Moreover, in the exemplary embodiment, plurality of support beams 1250 may be oriented along insertion axis 1404. Of course, in other embodiments, plurality of support beams 1250 could be oriented in any other directions.

In different embodiments, the spacing, or separation, between adjacent support beams could vary. In some embodiments, the spacing between adjacent support beams could be small relative to the lateral width of an implant. For example, the spacing could range between 0% and 10% of the width of an implant. In other embodiments, the spacing between adjacent support beams could be large relative to the width of an implant. For example, the spacing could range between 10% and 95% of the width of an implant (for example, two beams located adjacent to opposing lateral sides of the implant may could be spaced apart by 95% of the width of the implant). The spacing between adjacent beams (or between a beam and a portion of a peripheral structure) may be constant or may vary across an implant.

It may be appreciated that the relative spacing between support beams may be selected according to many factors, including the thicknesses of one or more support beams, the number of support beams used, the desired strength to weight ratio for an implant as well as other factors. Moreover, the spacing between adjacent support beams may be determined according to the dimensions of one or more bone contacting elements, since the bone contacting elements extend between adjacent support beams (or between a support beam and the peripheral structure).

In the embodiment shown in FIG. 21, each of support beam 1252, support beam 1254 and support beam 1256 are oriented in parallel with insertion axis 1404. This may help improve the strength of implant 1100 along the direction of insertion, since this is the direction where loads are applied during the OLIF surgical procedure.

In some embodiments, the geometry of the bone contacting elements may be configured to align with one or more axes. For example, in the embodiment shown in FIG. 21, the end portions of bone contacting element 1489 may be approximately oriented along the support beams (or other structures) to which they are attached. Specifically, first end portion 1491 is approximately oriented along support beam 1252 and second end portion 1492 is approximately oriented along support beam 1254 (i.e., the first and second end portions are aligned with insertion axis 1404). In contrast, intermediate portion 1490 may be oriented approximately along a direction parallel with posterior-anterior axis 1400. Moreover, while some bone contacting elements have intermediate portions arranged along posterior anterior axis 1400, other bone contacting elements have intermediate portions arranged in a direction parallel with second diagonal axis 1406. With this configuration, bone contacting elements may provide strength along multiple directions of the implant, including directions associated with insertion axis 1404, posterior-anterior axis 1400 and second diagonal axis 1406.

Figure 22:
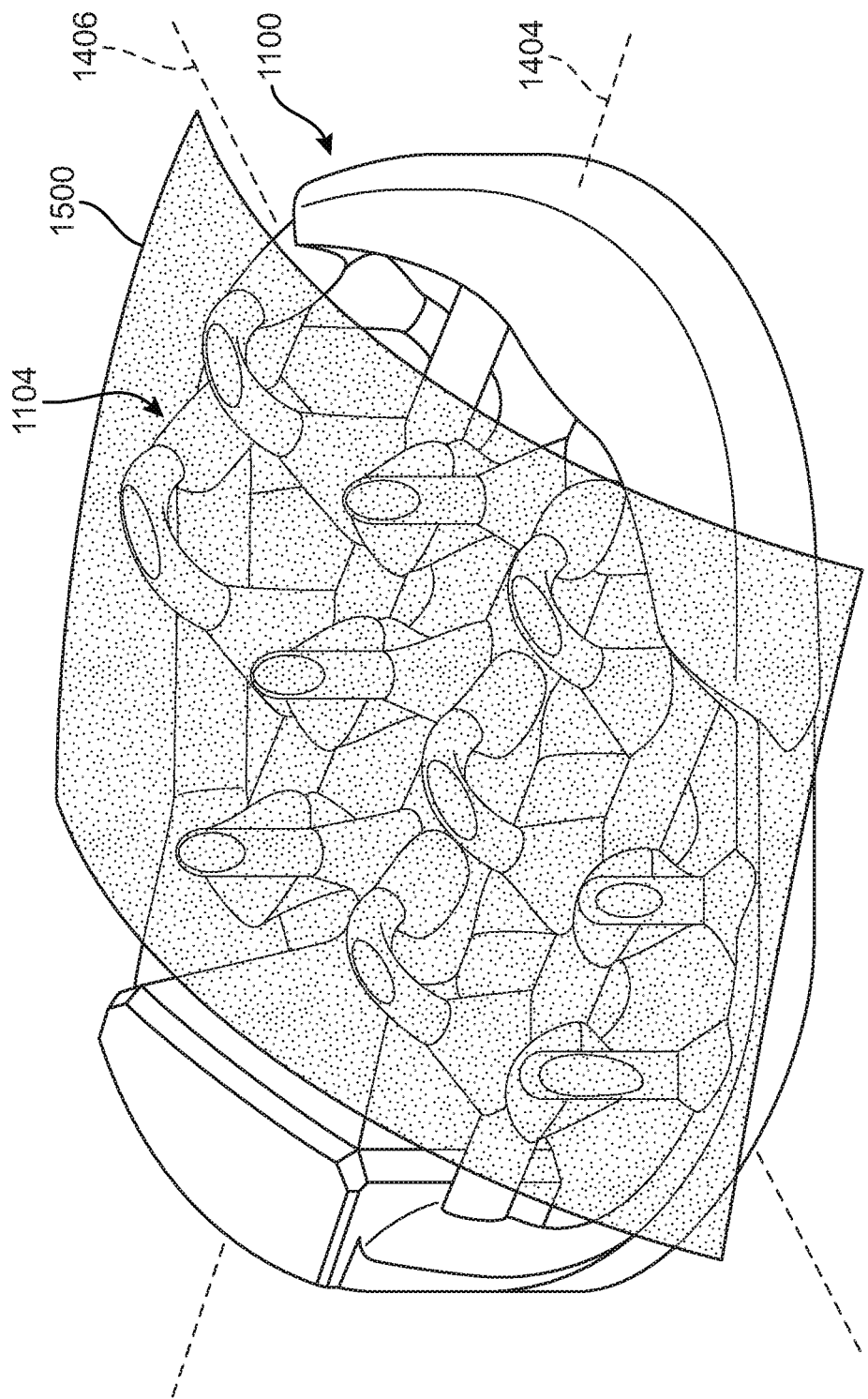
FIG. 22 is a schematic view of the implant of FIG. 18 with a curved plane indicating the convex geometry of a superior side of the implant.

Embodiments can include provisions to ensure a good fit with the endplates of adjacent vertebral bodies. As best seen in FIG. 22, which depicts a curved surface 1500 that is generally coincident with the superior surface of implant 1100, bone contacting elements 1104 may be configured to present generally convex superior and inferior surfaces that are curved along both insertion axis 1404 and second diagonal axis 1406. As seen in FIG. 22, curved surface 1500 generally curves down from second corner portion 1162 to fourth corner portion 1166. In some cases, curved surface 1500 may also curve slightly from first corner portion 1160 to third corner portion 1164.

This generally convex surface may be configured to fit a corresponding concave geometry in an adjacent vertebral endplate. Likewise, in some cases, the superior side of implant 1100 may be provided with a matching convex surface that fits a corresponding concave geometry in an adjacent vertebral endplate.

Figure 23:
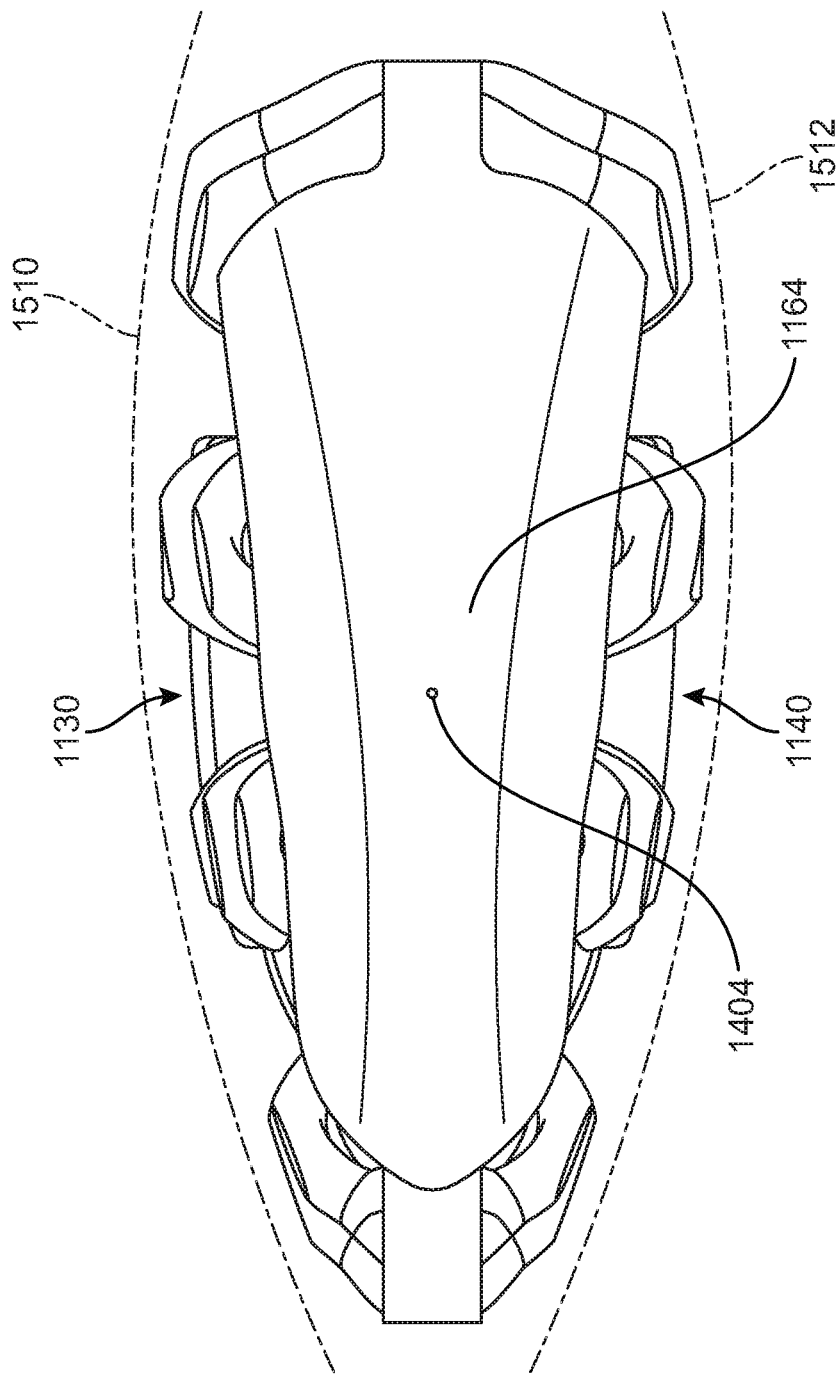
FIG. 23 is a schematic view of the implant of FIG. 18 showing the convex geometry of the superior and inferior sides.

As seen in FIG. 23, which shows a straight on view of third corner portion 1164 (i.e., a straight on view along insertion axis 1404), this curvature may be characterized by a convex curve 1510 along superior side 1130 and another convex curve 1512 along inferior side 1140.

Figure 24:
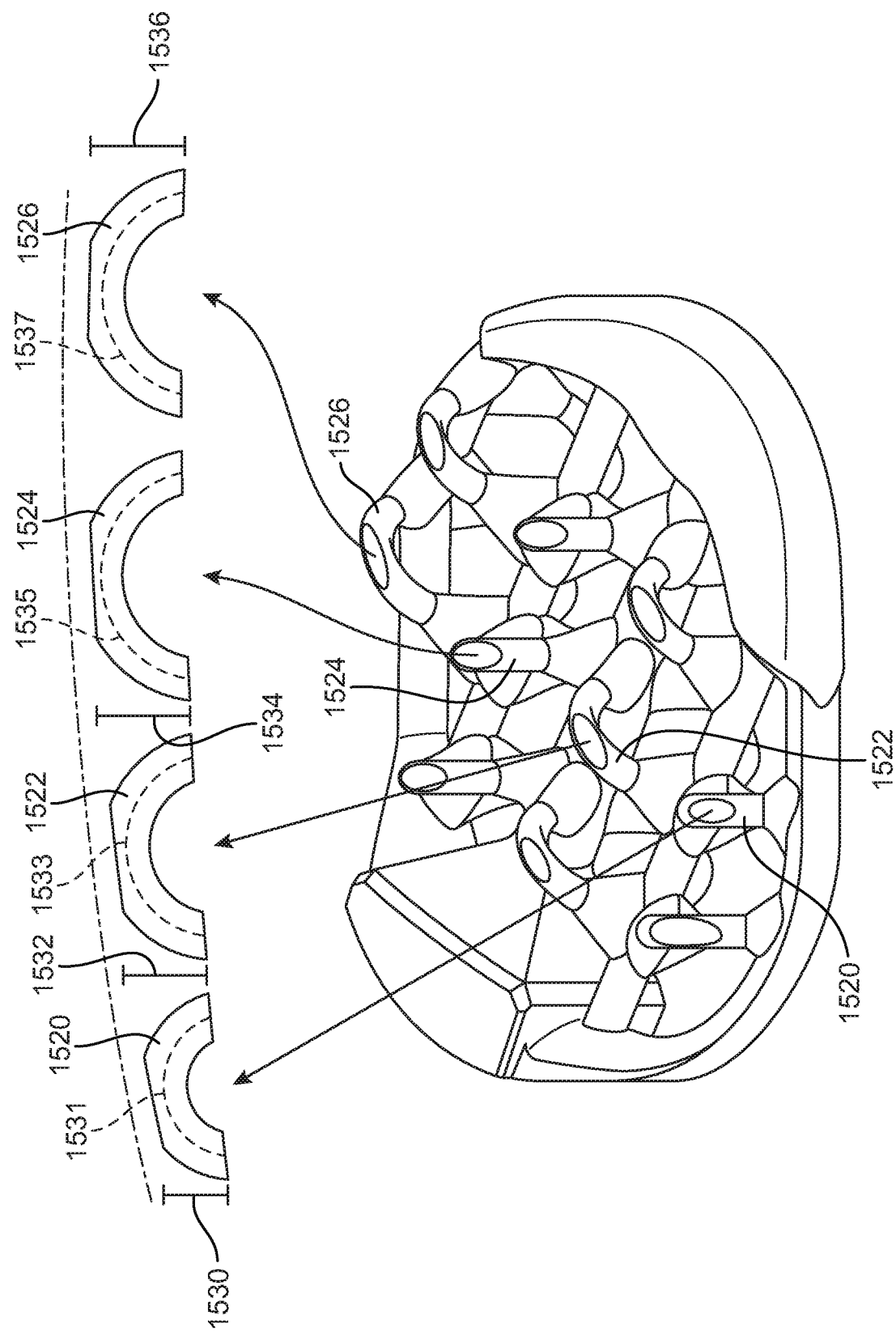
FIG. 24 is a schematic view of the implant of FIG. 18 including several enlarged schematic views of several bone contacting elements.

In some embodiments, this convex geometry may be achieved by varying the lengths (and thereby varying the heights) of bone contacting elements between second corner portion 1162 and fourth corner portion 1166. As seen in FIG. 24, which depicts a schematic view of four adjacent bone contacting elements, the height of an element may be proportional to its length. For example, a first bone contacting element 1520 has a first height 1530 and a first total length 1531. A second bone contacting element 1522 has a second height 1532 and a second total length 1533. A third bone contacting element 1524 has a third height 1534 and a third total length 1535. A fourth bone contacting element 1526 has a fourth height 1536 and a fourth total length 1537. Moreover, it may be seen that the heights generally increase from first height 1530 to third height 1534, and decrease again slightly to fourth height 1536. Likewise, the total lengths of each element vary in a corresponding manner, increasing from first total length 1531 to third total length 1535 and decreasing slightly again to fourth total length 1537.

It may be appreciated that implant 1100 may be configured with any of the provisions described above and shown in the embodiments of FIGS. 1-13. Such provisions may include textured surfaces, material construction and the use of bone growth promoting materials. Thus, in some embodiments, implant 1100 may be configured with a textured surface. In other embodiments, implant 1100 may be filled with bone growth promoting materials prior to insertion into a spine.

While various embodiments have been described, the description is intended to be exemplary, rather than limiting and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
a body comprised of a peripheral structure, a first support beam, a second support beam, and a third support beam;
a plurality of bone contacting elements attached to the body;
wherein the peripheral structure is further comprised of a first lateral portion, a second lateral portion, an anterior portion and a posterior portion;
wherein the first lateral portion and the anterior portion are joined at a first corner portion of the peripheral structure and wherein the second lateral portion and the posterior portion are joined at a second corner portion of the peripheral structure; and
wherein the first support beam has a first end attached to the first corner portion of the peripheral structure and wherein the first support beam has a second end attached to the second corner portion of the peripheral structure;
wherein at least one of the bone contacting elements bridges across a gap between the second support beam and the peripheral structure; and
wherein each support beam is in contact with an end of at least one of the plurality of bone contacting elements.

2. The implant according to claim 1, wherein the first support beam and the second support beam are arranged in parallel.

3. The implant according to claim 2, wherein the third support beam is arranged in parallel with the first support beam and the second support beam.

4. The implant according to claim 1, wherein the body includes an opening for receiving part of an insertion device.

5. The implant according to claim 4, wherein the opening is disposed in the first corner portion.

6. The implant according to claim 5, wherein the opening has a central axis and wherein the central axis of the opening is aligned with the first support beam.

7. The implant according to claim 5, wherein a posterior-anterior axis of the implant extends from the posterior portion to the anterior portion of the peripheral structure, and wherein the first support beam is oriented at an oblique angle with respect to the posterior-anterior axis.

\* \* \* \* \*